United States Patent
Kopf-Sill et al.

(10) Patent No.: US 6,858,185 B1
(45) Date of Patent: Feb. 22, 2005

(54) DILUTIONS IN HIGH THROUGHPUT SYSTEMS WITH A SINGLE VACUUM SOURCE

(75) Inventors: Anne R. Kopf-Sill, Portola Valley, CA (US); Steven A. Sundberg, San Francisco, CA (US); Andrea W. Chow, Los Altos, CA (US); Claudia L. Poglitsch, Sunnyvale, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 61 days.

(21) Appl. No.: 09/645,104

(22) Filed: Aug. 23, 2000

Related U.S. Application Data

(60) Provisional application No. 60/200,139, filed on Apr. 27, 2000, provisional application No. 60/159,014, filed on Oct. 12, 1999, and provisional application No. 60/150,670, filed on Aug. 25, 1999.

(51) Int. Cl.[7] ............................. G01N 33/00; B01L 3/02
(52) U.S. Cl. ....................... 422/100; 436/180; 436/52; 436/53; 436/179; 422/103
(58) Field of Search ................................ 436/179, 180, 436/52, 53; 422/100, 103

(56) References Cited

U.S. PATENT DOCUMENTS

| | | | |
|---|---|---|---|
| 4,390,403 A | | 6/1983 | Batchelder |
| 4,699,768 A | * | 10/1987 | Weiss ............................ 422/70 |
| 4,794,806 A | * | 1/1989 | Nicoli et al. ............. 73/863.01 |
| 4,908,112 A | | 3/1990 | Pace |
| 5,077,017 A | * | 12/1991 | Gorin et al. ................. 422/100 |
| 5,104,813 A | * | 4/1992 | Besemer et al. ............ 436/179 |
| 5,126,022 A | | 6/1992 | Soane et al. |
| 5,397,539 A | * | 3/1995 | Hayashi et al. ............... 422/65 |
| 5,498,392 A | | 3/1996 | Wilding et al. |
| 5,571,410 A | | 11/1996 | Swedberg et al. |
| 5,585,069 A | | 12/1996 | Zanzucchi et al. |
| 5,587,128 A | | 12/1996 | Wilding et al. |
| 5,593,838 A | | 1/1997 | Zanzucchi et al. |
| 5,603,351 A | | 2/1997 | Cherukuri et al. |
| 5,635,358 A | | 6/1997 | Wilding et al. |
| 5,637,469 A | | 6/1997 | Wilding et al. |
| 5,699,157 A | | 12/1997 | Parce |
| 5,750,015 A | | 5/1998 | Soane et al. |
| 5,779,868 A | | 7/1998 | Parce et al. |

(List continued on next page.)

FOREIGN PATENT DOCUMENTS

| | | | |
|---|---|---|---|
| WO | WO96/04547 | | 2/1996 |
| WO | WO97/02357 | | 1/1997 |
| WO | WO 98/00231 | * | 1/1998 |

(List continued on next page.)

OTHER PUBLICATIONS

Cohen, C.B. et al., "A Microchip–Based Enzymes Assay for Protein Kinase A," *Anal. Chem.* (1999) 273:89–97.

(List continued on next page.)

*Primary Examiner*—Monique T. Cole
(74) *Attorney, Agent, or Firm*—Donald R. McKenna

(57) ABSTRACT

Flow rates in a microfluidic device are modulated after performing serial dilutions by flow reduction channels that draw fluid from the main channel, thus reducing the flow rate. The reduction in flow rate and/or use of smaller dimension channels allow reduced reagent consumption. In addition, multiple flow reduction channels are used for multiple concentration measurements and for performing multiple assays simultaneously on a single sample. Also included are microfluidic devices and integrated systems for performing assays using serial dilutions, single pressure sources, multiple concentration measurements, and reduced reagent consumption. Devices comprising flow reduction channels are also used to suppress pressure perturbations from spontaneous injection.

13 Claims, 15 Drawing Sheets

U.S. PATENT DOCUMENTS

| | | | |
|---|---|---|---|
| 5,800,690 A | 9/1998 | Chow et al. | |
| 5,842,787 A | 12/1998 | Kopf-Sill et al. | |
| 5,852,495 A | 12/1998 | Parce | |
| 5,869,004 A * | 2/1999 | Parce et al. | 422/100 |
| 5,876,675 A | 3/1999 | Kennedy | |
| 5,880,071 A | 3/1999 | Parce et al. | |
| 5,882,465 A | 3/1999 | McReynolds | |
| 5,885,470 A | 3/1999 | Parce et al. | |
| 5,900,130 A * | 5/1999 | Benvegnu et al. | 204/453 |
| 5,922,591 A * | 7/1999 | Anderson et al. | 435/287.2 |
| 5,942,443 A | 8/1999 | Parce et al. | |
| 5,948,227 A | 9/1999 | Dubrow | |
| 5,955,028 A | 9/1999 | Chow | |
| 5,957,579 A | 9/1999 | Kopf-Sill et al. | |
| 5,958,203 A | 9/1999 | Parce et al. | |
| 5,958,694 A | 9/1999 | Nikiforov | |
| 5,959,291 A | 9/1999 | Jensen | |
| 5,964,995 A | 10/1999 | Nikiforov et al. | |
| 5,965,001 A | 10/1999 | Chow et al. | |
| 5,965,410 A | 10/1999 | Chow et al. | |
| 5,972,187 A | 10/1999 | Parce et al. | |
| 5,972,710 A * | 10/1999 | Weigl et al. | 436/34 |
| 5,976,336 A | 11/1999 | Dubrow et al. | |
| 5,989,402 A | 11/1999 | Chow et al. | |
| 6,001,231 A | 12/1999 | Kopf-Sill | |
| 6,004,515 A | 12/1999 | Parce et al. | |
| 6,011,252 A | 1/2000 | Jensen | |
| 6,012,902 A * | 1/2000 | Parce | 417/48 |
| 6,042,710 A | 3/2000 | Dubrow | |
| 6,046,056 A * | 4/2000 | Parce et al. | 204/403.05 |
| 6,068,752 A | 5/2000 | Dubrow et al. | |
| 6,071,478 A | 6/2000 | Chow | |
| 6,074,609 A * | 6/2000 | Gavin et al. | 422/99 |
| 6,074,725 A | 6/2000 | Kennedy | |
| 6,080,295 A | 6/2000 | Parce et al. | |
| 6,149,787 A | 11/2000 | Chow et al. | |
| 6,251,343 B1 * | 6/2001 | Dubrow et al. | 422/102 |
| 6,406,605 B1 * | 6/2002 | Moles | 204/601 |
| 6,416,642 B1 * | 7/2002 | Alajoki et al. | 204/451 |
| 6,500,323 B1 * | 12/2002 | Chow et al. | 204/450 |

FOREIGN PATENT DOCUMENTS

| | | | |
|---|---|---|---|
| WO | WO98/00231 | 1/1998 | |
| WO | WO98/00705 | 1/1998 | |
| WO | WO98/00707 | 1/1998 | |
| WO | WO98/02728 | 1/1998 | |
| WO | WO98/05424 | 2/1998 | |
| WO | WO 98/22811 | * 5/1998 | |
| WO | WO98/22811 | 5/1998 | |
| WO | WO98/45481 | 10/1998 | |
| WO | WO98/45929 | 10/1998 | |
| WO | WO98/46438 | 10/1998 | |
| WO | WO98/49548 | 11/1998 | |
| WO | WO98/55852 | 12/1998 | |
| WO | WO98/56505 | 12/1998 | |
| WO | WO98/56956 | 12/1998 | |
| WO | WO99/00649 | 1/1999 | |
| WO | WO99/10735 | 3/1999 | |
| WO | WO99/12016 | 3/1999 | |
| WO | WO99/16162 | 4/1999 | |
| WO | WO99/19056 | 4/1999 | |
| WO | WO99/19516 | 4/1999 | |
| WO | WO99/29497 | 6/1999 | |
| WO | WO99/31495 | 6/1999 | |
| WO | WO99/34205 | 7/1999 | |
| WO | WO99/43432 | 9/1999 | |
| WO | WO99/44217 | 9/1999 | |
| WO | WO99/56954 | 11/1999 | |
| WO | WO00/09753 | 2/2000 | |
| WO | WO00/45172 | 8/2000 | |
| WO | WO00/50172 | 8/2000 | |
| WO | WO00/50642 | 8/2000 | |
| WO | WO01/14064 | 3/2001 | |

OTHER PUBLICATIONS

Dasgupta, P.K. et al., "Electroosmosis: A Reliable Fluid Propulsion System for Flow Injection Analysis," *Anal. Chem.* (1994) 66:1792–1798.

Jacobson, S.C. et al., "Fused Quartz Substrates for Microchip Electrophoresis," *Anal. Chem.* (1995) 67:2059–2063.

Manz, A. et al., "Electroosmotic pumping and electrophoretic separations for miniaturized chemical analysis systems," *J. Micromech. Microeng.* (1994) 4:257–265.

Ramsey, J.M. et al., "Microfabricated chemical measurement systems," *Nature Med.* (1995) 1:1093–1096.

Seiler, K. et al., "Planar Glass Chips for Capillary Electrophoresis: Repetitive Sample Injection, Quantitation, and Separation Efficiency," *Anal. Chem.* (1993) 65:1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

Sundberg, S.A., "High–throughput and ultra–high–throughput screening: solution—and cell–based approches," *Current Opinions in Biotechnology* 2000, 11:47–53.

* cited by examiner

DILUTIONS IN HIGH THROUGHPUT SYSTEMS WITH A SINGLE VACUUM SOURCE

CROSS-REFERENCE TO RELATED APPLICATIONS

Pursuant to 35 U.S.C. § 119(e) and any other applicable statute or rule, the present application claims benefit of and priority to U.S. Ser. No. 60/150,670, entitled "Dilutions in High Throughput Systems with a Single Vacuum Source," filed Aug. 25, 1999 by Kopf-Sill et al.; U.S. Ser. No. 60/159,014, entitled "Dilutions in High Throughput Systems with a Single Vacuum Source," filed Oct. 12, 1999 by Kopf Sill et al.; and U.S. Ser. No. 60/200,139, entitled "Dilutions in High Throughput Systems with a Single Vacuum Source," filed Apr. 27, 2000 by Kopf-Sill et al.

BACKGROUND OF THE INVENTION

When carrying out chemical or biochemical analyses, assays, syntheses, or preparations one performs a large number of separate manipulations on the material or component to be assayed, including measuring, aliquotting, transferring, diluting, mixing, separating, detecting, etc. Microfluidic technology miniaturizes these manipulations and integrates them so that they can be performed within one or a few microfluidic devices.

For example, methods of performing dilutions in microfluidic devices were described in U.S. Pat. No: 5,869,004, by Parce and Kopf-Sill, "Methods and Apparatus for in Situ Concentration and/or Dilution of Materials in Microfluidic Systems." These methods successively draw off and add materials to microfluidic channels to serially dilute materials. The methods allow large accurate dilutions to be performed within the microscale environment.

For some bioassays, a constant flow of material is useful to maintain a fixed assay reaction time. Therefore, the ability to modulate a flow rate and obtain constant incubation and reaction times in a microfluidic system when performing dilutions would be useful to the integration of fluidic sample and reagent manipulations in a microfluidic assay format. In addition, a constant flow rate, e.g., in a microfluidic device with a single pressure source, would help to reduce the reagent usage for reagents added after the dilutions have been made.

Another technique that would be useful to integrate into a microfluidic format would be the ability to measure a sample at different concentrations simultaneously, to concurrently perform reactions at varying concentrations, and/or to test one sample concurrently versus a panel of different reagents.

Improved methods for controlling flow rates during dilutions and multiple concentration assays are, accordingly desirable, particularly those which take advantage of high-throughput, low cost microfluidic systems. The present invention provides these and other features by providing high throughput microscale systems for dilutions, reduced reagent consumption, multiple concentration measurements, and many other features that will be apparent upon complete review of the following disclosure.

SUMMARY OF THE INVENTION

The present invention provides devices and methods for modulating flow rates and reducing reagent consumption in microfluidic devices. In one aspect, the invention provides a device which includes flow reduction channels that are structurally configured to draw fluid from a main channel, thereby reducing the flow rate in the main channel.

In addition to providing flow rate modulation, these channels also provide for reduced reagent consumption by reducing the flow rate of the materials at the point of sample material introduction. Additional reduction in reagent consumption is optionally obtained by providing flow reduction channels of a smaller cross-sectional dimension than the main channel. Secondary flow reduction channels are also optionally added for additional reduction of reagent consumption.

In another aspect, the flow reduction channels provide a method of performing serial dilutions on a sample and obtaining measurements corresponding to each dilution level. The flow reduction channels provide a way to perform serial dilutions of a sample without increasing the flow rate with each dilution. Alternatively, one can change the cross-sectional area of the channel downstream of a mixing point. With a detection region provided in each flow reduction channel, measurements are optionally obtained at each dilution level.

In one aspect, the microfluidic devices of the invention comprise a body structure and a main pressure source. The body structure includes a main channel disposed therein, wherein the main channel is fluidly coupled to the main pressure source. The body structure also includes one or more flow reduction channels that intersect the main channel at one or more intersection points. The flow reduction channels are structurally configured to reduce fluid pressure or velocity in the main channel as the fluid flows past the one or more intersection point(s). In addition, the body structure can include a first pressure source fluidly coupled to the one or more flow reduction channels. The first pressure source is positioned on the one or more flow reduction channels downstream of the one or more intersection points in a direction of flow toward the first pressure source. In a preferred embodiment, the first pressure source and the main pressure source are the same, typically a single vacuum source fluidly coupled to the main channel at a position downstream from the flow reduction channel(s).

In another aspect, the microfluidic device comprises a body structure and a main pressure source, which is typically a single vacuum source. The body structure comprises a main channel disposed therein and fluidly coupled to the main pressure source. In addition, the body structure comprises one or more flow reduction channels that intersect the main channel at a first intersection point and a second intersection point, thus forming a bypass loop. The one or more flow reduction channels are structurally configured to reduce fluid pressure or velocity in the main channel as the fluid flows past the first intersection point in a direction toward the second intersection point. For example, typically the main pressure source is fluidly coupled to the main channel at a position downstream from the one or more flow reduction channels in a direction of flow toward the main pressure source.

The devices of the invention typically comprise 2 or more flow reduction channels in fluid communication with the main channel, but also optionally comprise about 3 to about 4 flow reduction channels or from about 5 to about 10 flow reduction channels or about 10 or more flow reduction channels. The cross-sectional dimension of the flow reduction channels is optionally the same as, larger than, or smaller than the cross-sectional dimension of the main channel.

In addition, the one or more flow reduction channels are optionally unintersected channels or intersected channels.

For example, the flow reduction channels are optionally intersected by sources or reservoirs for additional materials, such as reagents. In one embodiment, the flow reduction channels are intersected by secondary flow reduction channels, which are typically of smaller cross-sectional dimension than the flow reduction channels.

In other embodiments, the devices of the invention further comprise one or more detection regions within or proximal to the one or more flow reduction channels. The devices also optionally include a detection system comprising one or more detectors located proximal to the detection regions or to both the main channel and at least one of the one or more flow reduction channels. Preferably, a single detector is positioned to simultaneously detect a signal in each of the one or more flow reduction channels. Alternatively, the single detector scans across the various channels. A computer and software are optionally included in the devices for analyzing signals detected by the detection system. For example, the software can include instruction sets for detecting components of interest, their concentrations and the like.

In another embodiment, the device further comprises a source of a first fluidic material in fluid communication with the main channel at a first position along the main channel; and, a source of a second fluidic material in fluid communication with the main channel at a second position along the main channel. The sources of fluidic materials are typically upstream from at least one of the one or more flow reduction channels and are used to introduce fluidic materials into the device. The first fluidic material and the second fluidic material arc optionally the same or different materials, and typically comprise a sample material and a diluent or buffer material.

In another embodiment, the fluidic materials of the device are directed through the channels by a fluid direction system. The fluid direction system directs the movement of the first fluidic material and the second fluidic material from their sources to the main channel, thus combining the first fluidic material with the second fluidic material to form a third fluidic material. The fluid direction system also directs movement of a first portion of the third fluidic material from the main channel to a flow reduction channel, with a second portion of the third fluidic material remaining in the main channel. The second portion of the third fluidic material is then optionally directed through the main channel.

During operation of the device, the first fluidic material, e.g., a sample, has a first flow rate as it flows through the main channel. Upon addition of the second fluidic material, e.g., a buffer, to form the third fluidic material, e.g., a diluted sample, the flow rate in the main channel increases. Therefore, the third fluidic material or diluted sample has a second flow rate that is higher than the flow rate of the first fluidic material or sample. The second flow rate decreases after movement of the first portion of the third fluidic material from the main channel into a flow reduction channel. The second flow rate in one embodiment decreases to substantially the same level of the first flow rate, so that the device maintains a substantially constant flow rate.

In another embodiment, a device of the invention further comprises a source of a fourth fluidic material in fluid communication with the main channel at a third position, which third position is downstream of at least one of the one or more flow reduction channels. The fluid direction system directs movement of the fourth fluidic material from its source into the main channel. The fourth fluidic material is typically a reagent material that reacts with the third fluidic material, e.g., a diluted sample, to produce a product. One or more reagent materials, such as a substrate material and an enzyme, are optionally added to the device in this manner. The device provides reduced consumption of the reagent material by reducing the flow rate of the third fluidic material prior to the movement of the reagent material into the main channel.

Alternatively, reagent materials are added to the flow reduction channels. When the flow reduction channels are configured to have smaller cross-sectional dimensions than the main channel, the reagent consumption is reduced even farther. In addition, secondary flow reduction channels are optionally added to draw fluid from the flow reduction channels. Smaller dimensions in the secondary pressure channels reduce reagent consumption as well.

Methods for modulating a volumetric flow rate of a fluid in microfluidic devices are also provided. The method comprises providing a body structure, such as one described above, and flowing a first fluidic material through the main channel. A second fluidic material is flowed into the main channel, combining with the first fluidic material and resulting in a third fluidic material. A first portion of the third fluidic material is flowed through a flow reduction channel and a second portion of the third fluidic material is flowed through the main channel, thereby modulating the flow rate of the third fluidic material in the main channel and in the one or more flow reduction channels. These steps are optionally iteratively repeated to perform serial dilutions without substantially increasing the flow rate of materials within the channels.

In one embodiment, the method further comprises flowing the third fluidic material through a detection region which is optionally downstream of the position at which a fourth fluidic material is added to the main channel to react with the third fluidic material. By adding a fourth material after the flow rate has been reduced by the flow reduction channels, reagent consumption is decreased.

Additionally, the method provides for obtaining multiple measurements of a single sample, at multiple or repeat concentrations, or of a single sample, after undergoing multiple assays, by providing detectors proximal to each of the flow reduction channels. Alternatively, the channels are configured so that one detector detects signal from each of the channels, thereby concurrently measuring multiple concentrations or assay products.

In another embodiment, the present invention provides methods and devices to suppress pressure perturbations from spontaneous injection into a microfluidic device. The devices described above are optionally used to suppress pressure perturbations due to spontaneous injection. Spontaneous injection arises when samples are sipped into a microfluidic device through a capillary from an external sample source, e.g., one or more microwell plate.

Methods to reduce or eliminate pressure perturbations due to spontaneous injection comprise dipping an open end of a capillary into a sample source, thereby drawing a sample from the sample source into the capillary. The capillary, which is typically maintained at a first pressure, is fluidly coupled to a microfluidic device into which samples are flowed from the capillary. The method further comprises withdrawing the open end of the capillary from the sample source. A first portion of the sample remains on the open end and is spontaneously injected into the capillary due to the surface tension of the sample exerting a pressure on the capillary. From the capillary, the sample is flowed into the microfluidic device. A second portion of the sample is flowed from the capillary into a main channel, which intersects the capillary at a first intersection point. A third portion of the sample is flowed through a flow reduction or shunt channel, which intersects the main channel at the first intersection point or downstream of the first intersection point. Flowing a portion of the sample through a flow reduction channel creates a higher flow rate in the capillary than that needed in the main channel, thereby giving rise to a higher pressure gradient through the capillary. This higher pressure gradient in the capillary reduces the influence of the spontaneous injection pressure perturbation at the open end of the capillary, thereby suppressing pressure perturbations in the main channel.

In an example device to suppress spontaneous injection, the capillary comprises an inlet region and an outlet region. The inlet region, which is typically maintained at a first pressure, e.g., atmospheric pressure, is fluidly coupled to at least a first sample source during operation of the device and to a microfluidic body structure.

The body structure of the device typically comprises a plurality of microscale channels disposed therein. The microscale channels comprise a main channel having an upstream region and a downstream region. The upstream region of the main channel is fluidly coupled to the outlet region of the capillary at a first intersection point. In addition to the main channel, the devices include a shunt channel or flow reduction channel as described above. The shunt channel is fluidly coupled to at least the upstream region of the main channel and optionally to the downstream region of the main channel as well. A fluid direction system typically directs fluid from the outlet region of the capillary into the main channel and shunts a portion of the fluid into a shunt or by-pass channel, thereby reducing pressure perturbations in the main channel due to spontaneous injection into the main channel.

DETAILED DISCUSSION OF THE INVENTION

Figure 1:
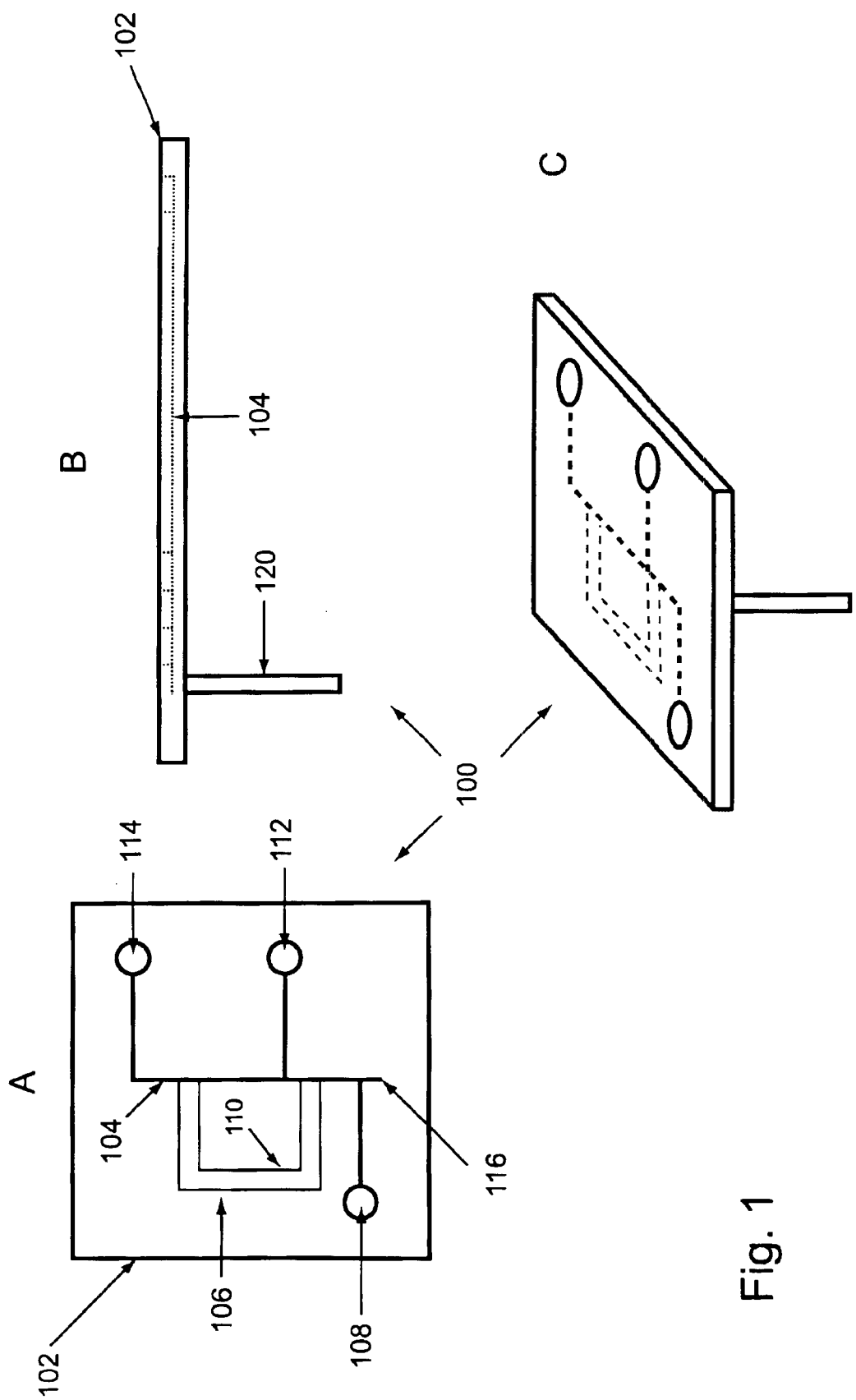
FIG. 1: Panels A, B, and C are schematic drawings of an integrated system of the invention, including a body structure, microfabricated elements, and a pipettor channel.

The present invention provides microfluidic methods and devices for modulating flow rates in microfluidic channel systems, particularly systems in which the flow of materials through the channels is pressure induced flow driven by a single pressure source. The invention provides devices containing flow reduction channels structurally configured to draw material from a main channel of the device during flow of the material in the main channel, thus reducing pressure, volumetric flow rate, and/or velocity in the main channel. In brief, the invention controls the flow rate by dividing the flow of material into multiple portions, which are all controlled by a single vacuum source.

The methods are also useful in providing suppression of spontaneous injection perturbations, e.g., when performed in a microfluidic device comprising a sipper capillary. For example, a sample is typically flowed from a microwell plate into a sipper capillary and then into a microfluidic channel, e.g., a main channel. Flowing a portion of the sample from the main channel into a flow reduction channel creates a pressure differential between the sipper capillary and the intersection point of the flow reduction channel and the main channel. This pressure differential suppresses pressure perturbations due to spontaneous injection of fluid from the tip of a sipper capillary into the microfluidic device.

In addition, the invention provides methods for simultaneously obtaining multiple concentration measurements on a single sample by simultaneously detecting the signal in the various flow reduction channels, e.g., by providing channels that converge in a single detection region. Therefore, the present invention allows serial dilutions and multiple concentration measurements to be obtained in a microfluidic device with a single vacuum source without substantially increasing the flow rate or increasing reagent consumption.

In other embodiments, the devices of the present invention are used to concurrently perform multiple assays on a single test compound. For example, a single sample is optionally divided into multiple portions and flowed into multiple parallel channels. Reagent wells fluidly coupled to each of the multiple channels are used to contact the various portions of sample with various reagents. A different reaction or assay, e.g., binding assay, is optionally carried out in each of the different channels. Alternatively, the same reaction is performed in each channel, the only difference being, e.g., a different enzyme isoform. By providing multiple channels that converge in a single detection region, the results of the various assays are optionally concurrently detected.

I. Microfluidic Devices Containing Flow Reduction Channels

In microfluidic devices, the volumes of sample materials of interest are extremely small, but in order to dilute the concentration of the materials, larger volumes of secondary materials, e.g., diluents, buffers, and the like, are added to the sample materials. The addition of larger volumes of fluids to microfluidic systems increases reagent consumption for reagents added to the samples after dilution, e.g., substrate and enzyme reagents are added to diluted inhibitor samples. For example, increased volume in the channels of a device in which the flow is driven by a single vacuum source causes an increased flow rate which increases the reagent consumption. The devices of the present invention solve this problem by drawing fluid from the channel in which the dilution takes place into a flow reduction channel. For example, as fluid is added to a main channel, e.g., to dilute a sample, the flow rate of fluid in the main channel increases. When a channel, e.g., a flow reduction channel or bypass loop, is positioned to intake a portion of the fluid from the main channel, the reduced amount of fluid in the main channel causes the flow rate to decrease, e.g., to its pre-dilution level. Thus, placement of channels in a microfluidic device provides reduced flow rates by removing fluid from a main channel. Additional flow rate reduction is optionally obtained, e.g., by drawing fluid from a flow reduction channel into a second flow reduction channel.

When the flow reduction channels are used in microfluidic sipper devices, e.g., devices comprising an external sipper capillary, to shunt fluid from the main channel, a pressure gradient is created with respect to the sipper capillary. This pressure gradient reduces pressure perturbations due to the spontaneous injection of fluid into the sipper capillary, e.g., as the capillary is moved from well to well of a microwell plate.

The configuration of flow reduction channels used in the present invention to control flow rate also provides devices for multiple concentration assays. Multiple concentration assays are accomplished by performing serial dilutions in a device comprising multiple flow reduction channels. After each dilution, a portion of the fluid is drawn from the main channel into a flow reduction channel. When multiple flow reduction channels are used after multiple dilutions, each flow reduction channel contains a different concentration of the sample material. The sample is then detected at multiple concentrations by one or more detectors.

Furthermore, reactions are optionally performed in the flow reduction channels by adding reagents to the flow reduction channels. This allows reactions to be carried out concurrently at the various sample concentrations, e.g., for determining enzyme kinetics in a high throughput system.

Alternatively, multiple assays are carried out in the flow reduction channels or parallel channel regions, e.g., at the same or different concentrations. Different reagents are optionally added to each channel to carry out different assays, e.g., on the same compound, e.g., which has been divided into multiple samples in the various flow reduction channels. Example applications include, but are not limited to, human serum albumin binding assays, genotyping assays, high throughput target screens, e.g., drug screening, selectivity screens, e.g., of a panel of different enzymes or isozymes, measurement of intrinsic drug fluorescence, and the like. The same assay is optionally repeated in each of the parallel channel regions, e.g., at a different concentration or the same concentration, for repeat measurements.

Additionally, the flow reduction channels provide for reduced reagent consumption in the assays due to the reduced flow rates. The flow reduction channels described above are typically incorporated into microfluidic devices and used as described below.

The devices generally comprise a body structure with microscale channels disposed therein. For example, the present system typically comprises, e.g., a main channel, one or more flow reduction channels, and one or more secondary flow reduction channels or reaction channels. The channels are fluidly coupled to each other and to various reservoirs or other sources of fluidic materials. Materials used in the present invention include, but are not limited to, buffers, diluents, substrate solutions, enzyme solutions, and sample solutions. In addition, the channels optionally comprise detection regions.

For example, various channels and channel regions are disposed throughout the microfluidic device. The devices typically include a main channel into which a sample is introduced. For example, a sample containing a potential modulator or activator of an enzyme of interest is introduced into a channel. An assay to determine the effect of the modulator, e.g., an activator or an inhibitor, on the enzyme's reaction rate is then optionally performed by allowing the enzyme to react with the substrate in the presence of the modulator. Reaction rates are often studied at multiple concentrations to determine the effect of concentration upon kinetic parameters. The devices of the present invention allow serial dilutions to be made in the microfluidic device without increasing the flow rate and thus minimize reagent consumption while maintaining constant reaction times for fixed channel lengths. In the present invention, devices are also provided for performing multiple concentration measurements simultaneously.

The flow and/or pressure reduction channels are channels that are structurally configured to reduce the pressure and/or flow rate in a main channel or in another flow reduction channel. A channel that is "structurally configured to reduce pressure/flow rate" is one that is configured to provide a desired flow rate. A device containing channels structurally configured to reduce pressure, flow rate, or velocity of the fluid in the channels typically relies on the structural configuration of the channels carrying the fluid to regulate the pressure and/or velocity in the channel, as opposed to relying on the modulation of forces such as a vacuum sources or electrokinetic forces. By configuring the channels to modulate the flow rate, a single constant driving force is optionally applied over the whole system, e.g., a single vacuum source.

For example, where a plurality of channels and a source of samples arc fluidly coupled, a single vacuum source can draw reagents from the source into the channels and move the sample through the channels. When channels are configured as in the present invention to serve as flow reduction channels, the vacuum will pull the fluid through the flow reduction channel as well as a main channel, thus dividing the flow into two portions and decreasing the velocity. Typically, the flow reduction channels in the present invention are spaced far enough apart that mixing of assay components is complete before part of the flow is diverted into the flow reduction channel.

Typically, the channel is configured by varying the channel length or cross section or by the addition of a flow-retarding matrix. These changes in the channel configuration alter the resistance to fluid flow in the channel, thus changing the flow rate. For example, by narrowing channel width, the flow rate is decreased by providing greater resistance to flow. A preferable way to structurally configure the channels to reduce fluid flow is to design or place a plurality of channels such that one channel, e.g., a pressure and/or flow reduction channel, pulls fluid from another channel, e.g., a main channel, thus decreasing resistance in the main channel. The flow rate of the materials in the channels is thus precisely modulated and reagent consumption is reduced by the appropriate configuration of flow reduction channels. By using one or more of the above methods, the channels are optionally structurally configured to reduce pressure or flow rate by a specific desired amount. For more detail on structurally configuring channels for desired flow rates using channel length and dimensions, see, e.g., U.S. Ser. No. 09/238,467, filed Jan. 28, 1999.

In the present invention, the reduction in flow rate and/or pressure is typically accomplished by drawing fluid from the main channel into a flow reduction channel or a shunt channel, e.g., by tapping off pressure. Secondary flow reduction channels are those flow reduction channels that draw fluid from another flow reduction channel. These secondary flow reduction channels are preferably of smaller cross-sectional dimension than the channels from which they draw fluid. In this case, the channels optionally function as reaction channels when they are fluidly coupled to sources of reagent materials. This type of reaction channel provides reduced reagent consumption because the flow rate has been reduced and the dimension of the channel is reduced so that smaller amounts of reagents are required to perform the assays of interest.

Alternatively, the channels in the present invention are configured to provide assay channels, e.g., for performing multiple assays on a single compound. For example, a microfluidic device is optionally configured to provide multiple parallel channels. A single sample is optionally sipped into the device through a capillary fluidly connected to the parallel channels. The sample is optionally divided into portions, each of which is flowed through a separate parallel channel region. A different assay is then optionally performed on each of the sample portions, e.g., by using different channel chemistries or by adding different reagents into each channel. For example, different channels are optionally loaded with various bead arrays comprising different chemistries or with different separation matrices. In other embodiments, individual channels comprise different surface modifications, e.g., to provide different chemistries in each channel.

The term "downstream" refers to a location in a channel or microfluidic device that is farther along the channel or plurality of channels in a selected direction of fluid or material flow, relative to a selected site or region. For example, the pressure source is optionally farther along in the direction of flow in the channel system than the buffer well or flow reduction channels; therefore, the fluid flows down the main channel past the buffer well and past the flow reduction channels towards the pressure source. In this embodiment, the pressure source is typically a vacuum source.

In another embodiment of the present device, the pressure source is optionally positioned at the upstream end of the main channel. "Upstream" refers to a location in a channel or system of channels that is farther along the channel or plurality of channels in a direction that is opposite the flow of fluid or material flow, relative to a selected site or region. For example, a pressure source is optionally upstream from the detection region. The pressure source is optionally positioned at the sample well, where sample materials are introduced into the system. In this instance, the pressure source would push the fluid through the channels in a direction away from the pressure source and toward the opposite end of the channel, e.g., the detection region or waste well.

Reservoirs or wells are locations at which samples, components, reagents and the like are added into the device for assays to take place. Introduction of these elements into the system is carried out as described below. The reservoirs are typically placed so that the sample or reagent is added into the system upstream from the location at which it is used. For example, a dilution buffer will be added upstream from the source of a reagent if the sample is to be diluted before reaction with the reagent.

In the present case, a dilution buffer is typically added into the main channel upstream of a flow reduction channel, so that the increase in flow rate due to the addition of buffer material may be counteracted by the reduction in pressure due to the flow reduction channel. Reagent materials, on the other hand, are typically added downstream of a flow reduction channel so that they are added after the flow rate has been reduced so that smaller quantities of reagent are added.

In some embodiments, a different reagent well or multiple reagent wells are fluidly coupled to each of the flow reduction channels or to each channel or channel region, e.g., in a parallel channel configuration. The reagent wells in this case, are optionally used to add a different reagent or reagents to each channel, e.g., to perform a different assay in each channel, e.g., to concurrently assay multiple binding sites on a single target or to screen a variety of enzyme isoforms.

Detection regions are also included in the present devices. The detection region is optionally a subunit of a channel or of multiple channels that are close in space, or it optionally comprises a distinct channel that is fluidly coupled to the plurality of channels in the microfluidic device. The detection region is optionally located proximal to the main channel. For example, in FIG. 5, detection region 532 is proximal to main channel 504. Alternatively, detection regions are positioned proximal to one or more of the flow reduction channels, such as in FIG. 6 where detection regions 634, 636, and 638 are proximal to flow reduction channels 612, 610, and 608 respectively. In another embodiment, detection regions are placed proximal to one or more of the secondary flow reduction channels. For example, detection regions 734, 736, and 738 are proximal to secondary flow reduction channels 742, 744, and 746.

Alternatively, the detection region may comprise a region that is proximal to all of the flow reduction channels and the main channel in the device. For example, the detection region is optionally located at a point downstream of the main channel and all the flow reduction channels so that it is proximal to both the main channel and the flow reduction channels. Such a device is depicted in FIG. 8. When the flow reduction channels and the main channel are configured such that they all converge, then one detection region is sufficient for detection of signals from all the proximal channels. For example, multiple assays are optionally performed in multiple parallel channels, e.g., on a single sample under different assay conditions or at various concentrations, and the results are optionally concurrently detected in a single detection region in which all of the multiple channel regions converge.

The detection window or region at which a signal is monitored typically includes a transparent cover allowing visual or optical observation and detection of the assay results, e.g., observation of a colorimetric or fluorometric signal or label. Such regions optionally include one or more detectors. Examples of suitable detectors for use in the detection regions are well known to those of skill in the art and are discussed in more detail below.

The elements described above, including but not limited to, flow reduction channels, bypass loops, detection regions, and reservoirs are optionally combined into microfluidic devices that are useful in controlling flow rates, reducing reagent consumption, and performing multiple concentration measurements or multiple assays, e.g., on a single sample. Specific examples of channel configurations are provided in the figures, which are described below. Other possible configurations using substantially the same elements will be apparent upon review of the entire disclosure.

Figure 3:
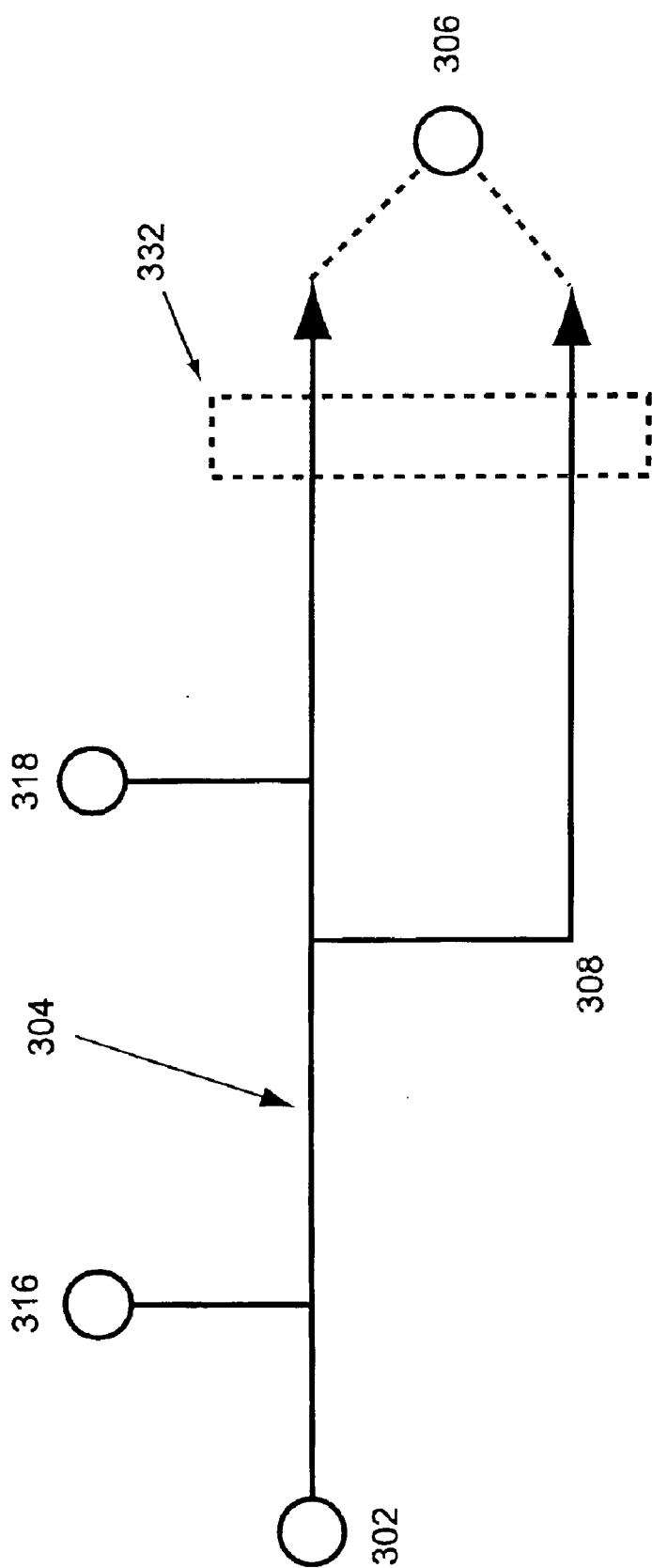
FIG. 3: Schematic drawing of a microfluidic device comprising a single flow reduction channel.

One embodiment of a device of the present invention is illustrated in FIG. 3. As shown, the device comprises sample well 302, which is used to introduce a sample or fluidic material into the device. From sample well 302, the fluidic material is flowed through main channel 304. Additional materials are optionally added to the fluidic material as it flows through main channel 304. For example, a buffer is optionally added to dilute the fluidic material. In addition, a reagent is optionally added to the fluidic material, which reacts with the reagent to form a product. The fluidic material is flowed through the device using, e.g., pressure source 306, which is optionally located at the downstream end of the main channel. Alternatively the pressure source is located at sample well 302. In the configuration shown in FIG. 3, pressure source 306 is fluidly coupled to main channel 304 at the downstream end. When a second fluidic material, e.g., a dilution buffer, is added to the fluidic material in main channel 304, the flow rate of the fluidic material in main channel 304 increases. To decrease the flow rate in the main channel, a first portion of the fluidic material is flowed into flow reduction channel 308. Flow reduction channel 308 is configured to draw fluid from main channel 304 and reduce the pressure and/or velocity in main channel 304. In this embodiment, flow reduction channel 308 is fluidly coupled at its downstream end to pressure source 306.

The reduction in pressure or velocity in main channel 304 serves multiple purposes. In one embodiment, the flow reduction reduces the volumetric flow rate and thus reduces the amount of reagent that must be added to main channel 304 in any reactions carried out downstream of flow reduction channel 308. For example, a reagent that is used in an assay with the fluidic material is optionally added through reagent well 318. Smaller amounts of reagent from reagent well 318 are required after the flow rate has been decreased by drawing fluid into flow reduction channel 308.

Alternatively, the flow reduction allows multiple concentrations of the same sample material to be measured in one device. For example, a dilution buffer is optionally added from buffer well 316 to the sample introduced from sample well 302. A first portion of the resulting fluid is then drawn from main channel 304 into flow reduction channel 308 and detected in detection region 332. Simultaneously, a second portion of the resulting fluid is flowed through main channel 304, where it is again diluted with a dilution buffer from reagent well 318, resulting in a successive dilution of the sample material. This diluted material is then flowed through main channel 304 and detection region 332, where it is detected concurrently with the first dilution.

Figure 4:
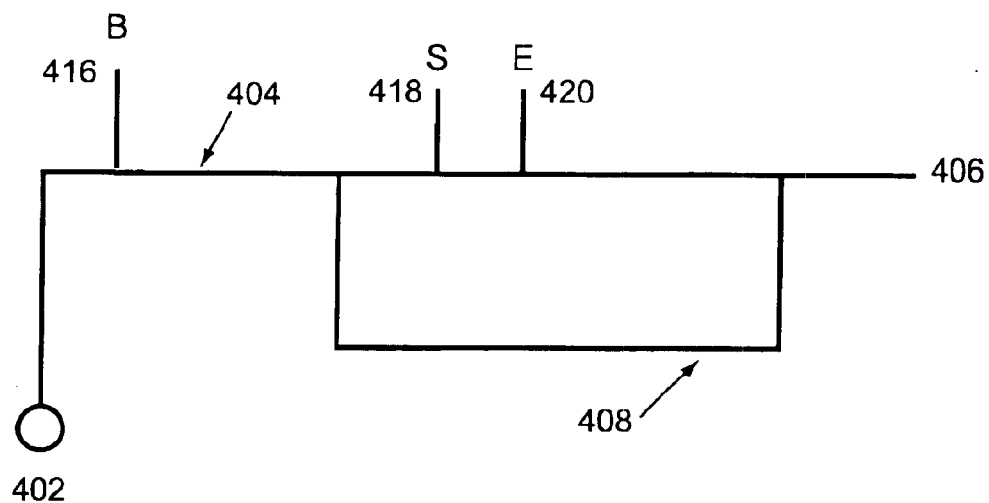
FIG. 4: Schematic drawing of a microfluidic device comprising a single flow reduction channel in a bypass loop configuration.

In another embodiment, shown in FIG. 4, flow reduction channel 408 is structurally configured to draw fluid from main channel 404 by forming a bypass loop off main channel 404. This embodiment works in substantially the same way as that in FIG. 3. For example, fluid is flowed from sample well 402 into main channel 404. Additional fluid is then added from reservoir 416 and then a portion of the fluid is drawn from main channel 404 into flow reduction channel 408, thereby reducing the pressure in main channel 404 and reducing the flow rate of fluid. The fluid flow is typically controlled by vacuum source 406, but is optionally any other type of pressure control system that draws fluid through or into main channel 404.

Figure 5:
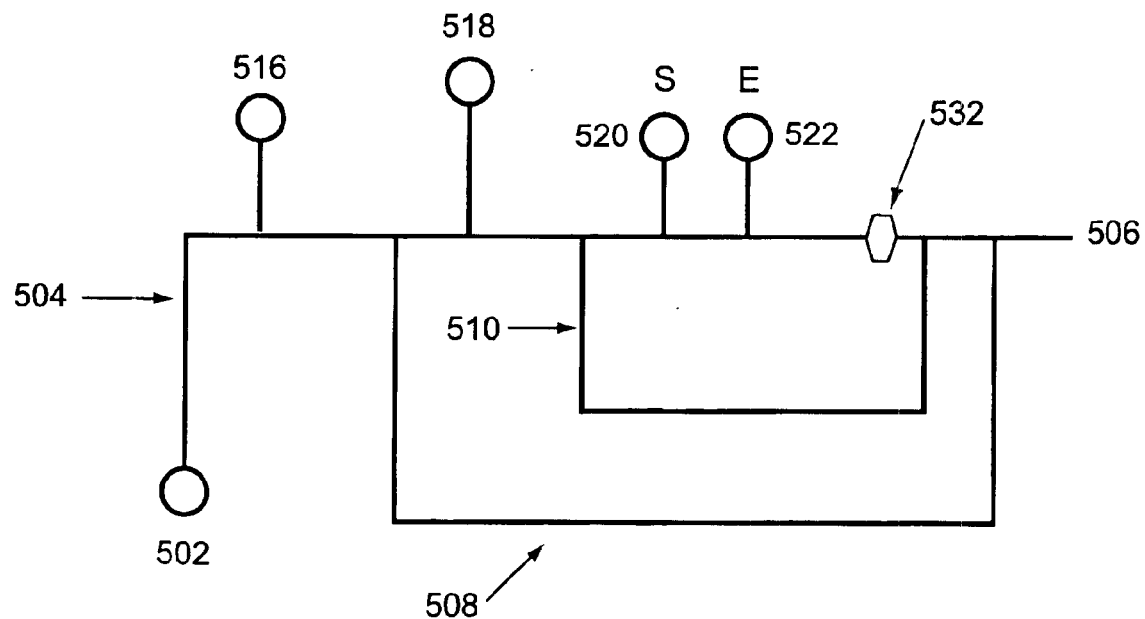
FIG. 5: Schematic drawing of a microfluidic device comprising multiple flow reduction channels, e.g., for use in making serial dilutions of a single sample or for performing multiple assays on a single sample.

FIG. 5 illustrates an alternate embodiment of the device in FIG. 4, in which multiple flow reduction channels are included in the device. For example, samples are introduced into the device through sample well 502, and transported through main channel 504. At this point, multiple dilutions are optionally performed in the device of FIG. 5. For example, a dilution buffer is added to the sample through reservoir 516, resulting in a diluted sample, at which point the flow rate and/or pressure in main channel 504 increases. The pressure is reduced by drawing a portion of the diluted fluid into flow reduction channel 508. An additional dilution is optionally made by adding dilution buffer into the main channel from reservoir 518, resulting in a second diluted sample. At this point, the pressure in main channel 504 is again increased, thus increasing the flow rate. Therefore, flow reduction channel 510 (the second flow reduction channel or bypass loop) is used to reduce the pressure, thus controlling the flow rate in main channel 504. More dilutions are optionally made at this point, with pressure controlled by additional flow reduction channels. After the desired dilution concentration is obtained, the sample is optionally reacted with a variety of reagents that may be added to the sample through reservoirs 520 and/or 522. The sample is also optionally detected by a detector placed proximal to detection region 532.

Figure 6:
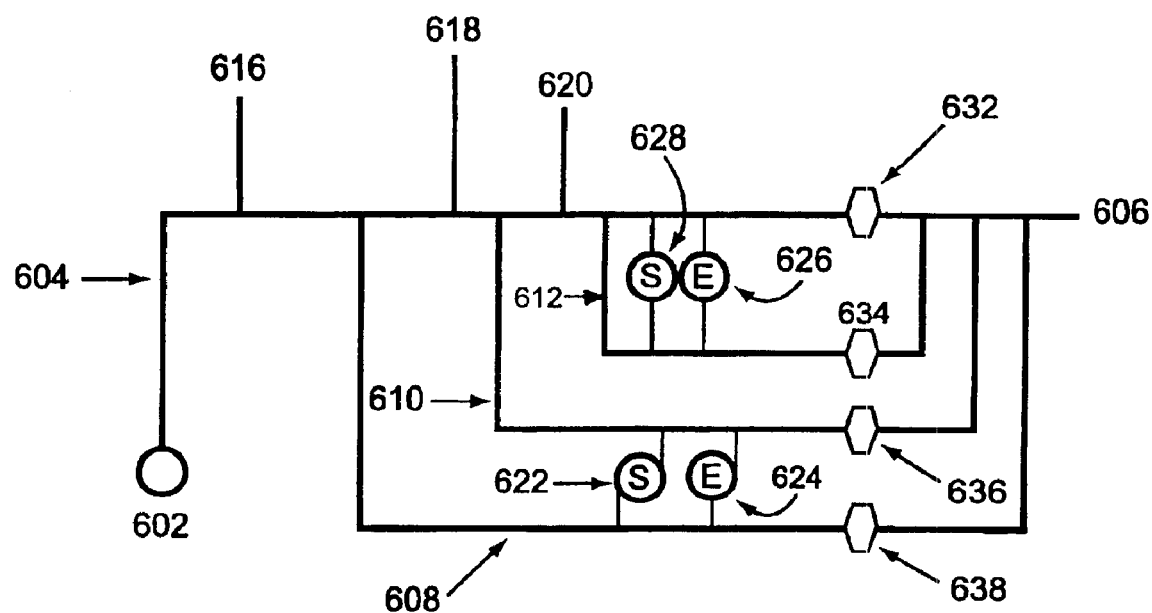
FIG. 6: Schematic drawing of a microfluidic device comprising multiple flow reduction channels, multiple detectors, and multiple reagent wells, e.g., for obtaining multiple concentration measurements on a single sample or for assaying multiple test compounds or enzymes against a single sample.

FIG. 6, showing an additional embodiment of FIG. 4, provides a device in which assays are optionally run on the same sample at various concentrations and simultaneously detected. The device in FIG. 6 works like the one in FIG. 5 described above with an additional dilution step possible due to the addition of flow reduction channel 612 (in addition to flow reduction channels 608 and 610). Furthermore, the device of FIG. 6 contains detection regions 632, 634, 636, and 638, which are positioned proximal to main channel 604, and flow reduction channels 612, 610, and 608 respectively. Thus, detectors placed proximal to detection regions 632, 634, 636, and 638 are optionally used to detect fluid as it flows through main channel 604, and flow reduction channels 608, 610 and 612, which, when configured and operated as described above, contain various concentrations of the sample material that was injected or sipped at sample well 602. Alternatively, flow reduction channels 608, 610 and 612 are optionally used to perform a different assay on the same sample, a portion of which is flowed through all three channels. Reagents for each assay are added to the flow reduction channels, e.g., from reservoirs 622, 624, 626, and/or 628.

In addition, FIG. 6 comprises additional reservoirs 622, 624, 626, and 628 for adding materials, e.g., reagents, such as substrates and enzymes, into main channel 604 and flow reduction channels 608, 610 and 612. Thus, an assay of interest is optionally performed at all of the various concentrations of sample material in the flow reduction channels. Furthermore, the reagent usage is decreased by the decrease in flow rate produced by the flow reduction channels.

Figure 7:
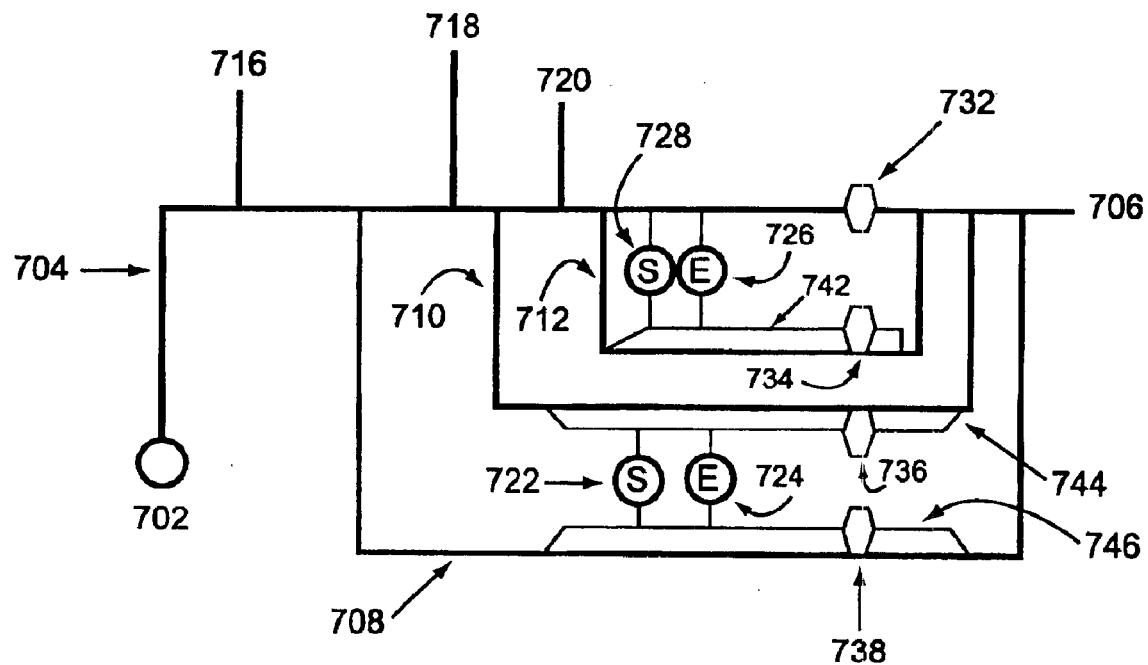
FIG. 7: Schematic drawing of a microfluidic device comprising multiple flow reduction channels and secondary flow reduction channels, e.g., for obtaining multiple concentration measurements on a single sample and reducing reagent consumption.

An additional embodiment of the invention provides an even greater reduction in reagent usage by varying the channel dimensions in which the assays of interest are performed. For instance, FIG. 7 illustrates a device in which flow reduction channels of smaller dimension are added as bypass loops. For example, secondary flow reduction channels 742, 744, and 746 are fluidly coupled to flow reduction channels 708, 710, and 712. The secondary flow reduction channels function to reduce pressure and/or velocity in flow reduction channels 708, 710, and 712 by drawing fluid out of the flow reduction channels. Secondary flow reduction channels 742, 744, and 746 therefore reduce reagent consumption by decreasing flow rate in the channels.

In addition, secondary flow reduction channels 742, 744, and 746 reduce reagent consumption even more when used as reaction channels. As reaction channels, they are typically configured to have a smaller cross-sectional dimension than flow reduction channels, e.g., flow reduction channels 708, 710, and 712. Reservoirs 722, 724, 726, and 728 are fluidly coupled in this embodiment to secondary flow reduction channels 742, 744, and 746, so that the amount of reagents added from the reservoirs into the smaller dimension channels is smaller. Additionally, detection regions 732, 734, 736 and 738 are located proximal to secondary flow reduction channels 742, 744, and 746 for detection of materials in those channels. Thus assays of interest are optionally performed on small volumes, to reduce reagent consumption, and at various dilution levels concurrently and then concurrently detected at those levels. Furthermore the detection regions in the various flow reduction channels are optionally configured in such as way that one detector may be used to detect signals from all flow reduction channels and the main channels simultaneously.

FIG. 8, Panels A and B, provides a schematic illustration and an actual embodiment of one possible channel configuration in which fluid in the various flow reduction channels, secondary flow reduction channels, and the main channels are detectable by the same detector. Other configurations are also possible. The devices in FIG. 8 provide capillary attachment point 802, 802B positioned on the main channel. Samples are introduced into a device at capillary attachment point 802, 802B. The sample is flowed into parallel channel regions 808, 808B, 810, 810B, 812, 812B, and main channel region 804, 804B. These channels act as flow reduction channels in that they are structurally configured to reduce volumetric flow rate in main channel region 804, 804B, by drawing fluid from main channel region 804, 804B into parallel channel regions 808, 808B, 810, 810B, and 812, 812B. The fluid in channel regions 808, 808B, 810, 810B, and 812, 812B is optionally diluted with material from reservoirs 816, 816B and 818, 818B, which are fluidly coupled to channel regions 808, 808B, 810, 810B, 812, 812B, 844, 846, 848, 850 and 852. After the dilutions, the pressure and/or flow rate is optionally further reduced by secondary flow reduction channels (or reaction channels) 842, 844, 846, 848, 850, and 852. By utilizing all of the secondary flow reduction channels available, multiple serial dilutions are optionally made without significantly increasing the flow rate of the fluid through main channel region 804 and parallel channel regions 808, 810, and 812. After the desired dilution level is achieved, assays are optionally performed at multiple dilution levels, such as those obtained in channel regions 804, 804B, 808, 808B, 810, 810B, 812, 812B, 842, 844, and 846. The result of the various assays or concentration levels is detected concurrently because channel regions 804, 804B, 808, 808B, 810, 810B, 812, 812B, 842, 844, and 846 all converge in detection region 832, 832B, before being discarded in waste well 806, 806B. In an additional embodiment, a single pressure source is optionally applied at waste well 806, 806B for inducing flow through the channel system.

Figure 8A:
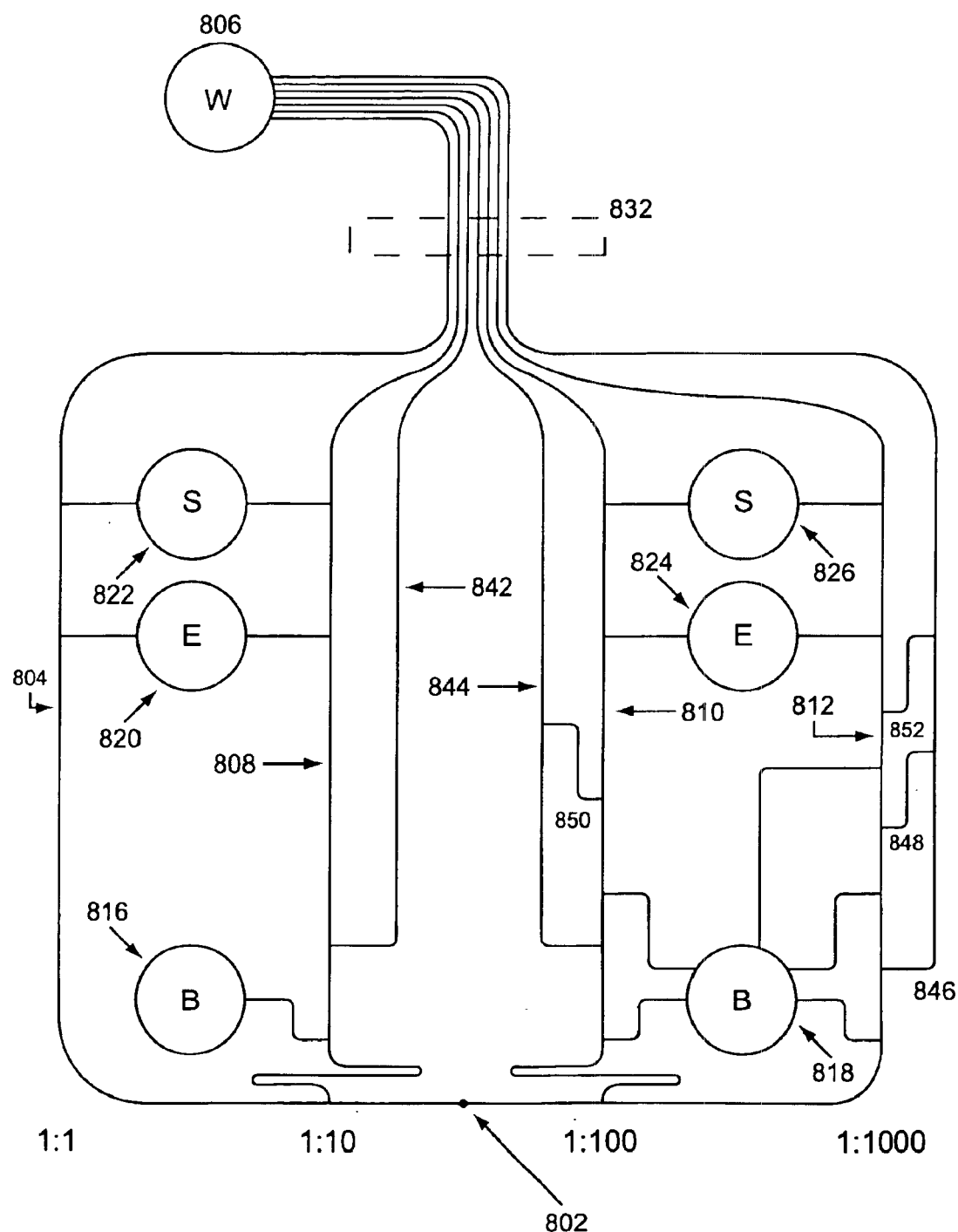
FIG. 8: Panel A provides a schematic drawing of a microfluidic device comprising multiple flow reduction channels configured in parallel and fluidly coupled to a single detection window, e.g., for simultaneously obtaining multiple measurements on a single sample, e.g., at various concentrations or for different assay conditions. Panel B depicts one possible embodiment of a channel configuration corresponding to the schematic of Panel A.
Figure 8B:
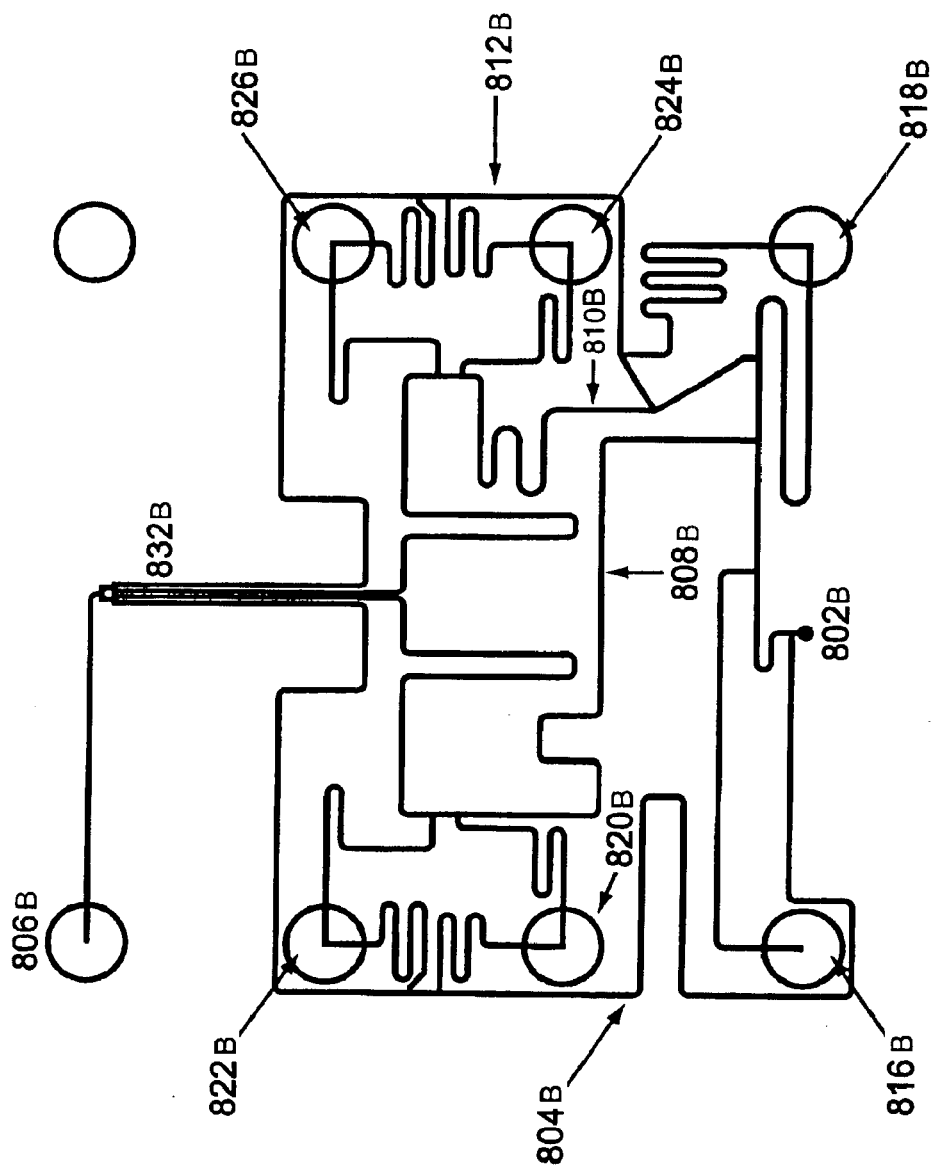

In one embodiment, the parallel channel configuration of FIGS. 8A and 8B is used to perform multiple assays, e.g., on the same test compound or on different test compounds. For example, a test compound, e.g., a single test compound, is optionally sipped from a capillary, e.g., from a microwell plate, into a microfluidic device as shown in FIG. 8A. The compound is then optionally divided into four portions. One portion is flowed through parallel channel region 804. A second portion is flowed through parallel channel region 808, a third portion through channel region 810, and a fourth portion through channel region 812. Each sample portion is then optionally subjected to a different assay. For example, reservoir 820 is optionally used to add reagents necessary for an assay to probe binding site I in a human serum albumin (HSA) assay in channel 804 and reservoir 822 is used to add reagents necessary to probe binding site II in an HSA assay in channel 808. Reservoirs 824 and 826 are also optionally used to add reagents for other assays into channels 810 and 812. Alternatively, the reservoirs add the same reagents to each channel, so that the same assay is performed to obtain repeat measurements, e.g., four times, or the same assay at different concentrations. In other embodiments, the same reaction is performed in each channel, the only difference being, e.g., a different enzyme isoform. The results of the different assays are then optionally concurrently detected in detection window 832.

A variety of microfluidic devices are optionally adapted for use in the present invention by the addition of flow reduction components as described above. These devices are described in various PCT applications and issued U.S. Patents by the inventors and their coworkers, including U.S. Patent Nos. 5,699,157 (J. Wallace Parce) issued Dec. 16, 1997, U.S. Pat. No. 5,779,868 (J. Wallace Parce et al.) issued Jul. 14, 1998, U.S. Pat. No. 5,800,690 (Calvin Y. H. Chow et al.) issued Sep. 1, 1998, U.S. Pat. No. 5,842,787 (Anne R. Kopf-Sill et al.) issued Dec. 1, 1998, U.S. Pat. No. 5,852,495 (J. Wallace Parce) issued Dec. 22, 1998, U.S. Pat. No. 5,869,004 (J. Wallace Parce et al.) issued Feb. 9, 1999, U.S. Pat. No. 5,876,675 (Colin B. Kennedy) issued Mar. 2, 1999, U.S. Pat. No. 5,880,071 (J. Wallace Parce et al.) issued Mar. 9, 1999, U.S. Pat. No. 5,882,465 (Richard J. McReynolds) issued Mar. 16, 1999, U.S. Pat. No. 5,885,470 (J. Wallace Parce et al.) issued Mar. 23, 1999, U.S. Pat. No. 5,942,443 (J. Wallace Parce et al.) issued Aug. 24, 1999, U.S. Pat. No. 5,948,227 (Robert S. Dubrow) issued Sep. 7, 1999, U.S. Pat. No. 5,955,028 (Calvin Y. H. Chow) issued Sep. 21, 1999, U.S. Pat. No. 5,957,579 (Anne R. Kopf-Sill et al.) issued Sep. 28, 1999, U.S. Pat. No. 5,958,203 (J. Wallace Parce et al.) issued Sep. 28, 1999, U.S. Pat. No. 5,958,694 (Theo T. Nikiforov) issued Sep. 28, 1999, and U.S. Pat. No. 5,959,291 (Morten J. Jensen) issued Sep. 28, 1999; and published PCT applications, such as, WO 98100231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, and WO 99/44217.

For example, pioneering technology providing cell based microscale assays are set forth in U.S. Pat. No. 5,942,443, by Parce et al. "High Throughput Screening Assay Systems in Microscale Fluidic Devices" and, e.g., in 60/128,643 filed Apr. 4, 1999, entitled "Manipulation of Microparticles In Microfluidic Systems," by Burd Mehta et al. Complete integrated systems with fluid handling, signal detection, sample storage and sample accessing are available. For example, U.S. Pat. No. 5,942,443 provides pioneering technology for the integration of microfluidics and sample selection and manipulation.

In addition, various other elements are optionally included in the device, such as particle sets, separation gels, antibodies, enzymes, substrates, and the like. These optional elements are used in performing various assays. For example, in a kinase reaction a product and substrate are typically separated electrophoretically, e.g., on a separation gel. Cell based microscale assays are also optionally performed in the devices of the invention. With cell assays, for example, a constant flow rate is important for ascertaining and modulating cell incubation times. Cell-based microscale systems are set forth in Parce et al. "High Throughput Screening Assay Systems in Microscale Fluidic Devices" WO 98/00231 and, e.g., in 60/128,643 filed Apr. 4, 1999, entitled "Manipulation of Microparticles In Microfluidic Systems," by Mehta et al.

Complete integrated systems with fluid handling, signal detection, sample storage and sample accessing are also available. For example WO 98/00231 (supra) provides pioneering technology for the integration of microfluidics and sample selection and manipulation.

Also included in the integrated systems of the invention are sources of sample materials, enzymes, and substrates. These fluidic materials are introduced into the devices by the methods described below.

Sources of Assay Components and Integration with Microfluidic Formats

Reservoirs or wells are provided in the present invention as sources of buffers, diluents, substrates, enzymes, reagents, and the like. For example, FIG. 3 illustrates various reservoirs, such as sample wells 302, buffer well 316, and reagent well 318. These reservoirs are fluidly coupled to main channel 304. FIG. 6 illustrates alternate placement of reagent wells, such as reservoirs 622, 624, 626, and, 628. These reservoirs are positioned so that they are fluidly coupled to flow reduction channels 608, 610, and 612. In FIG. 8A, for example, reservoirs 820, 822, 824, and 826 each optionally comprise a different reagent, e.g., for performing different assays in channels 804, 808, 810, and 812. In other embodiments, the different assay channels are fabricated or pre-filled with different reagents to conduct a different assay in each channel. For example, channels 804, 808, 810, and 812 are each exposed to or filled with a different reagent either before to during the assay. Different chemistries are achieved in each channel using, e.g., beads comprising different reagents, e.g., having different properties, separation matrices, e.g., gels, and/or reagents that modify or react with the channel surface.

Sources of samples, buffers, and reagents, e.g., substrates, enzymes, and the like, are fluidly coupled to the microchannels noted herein in any of a variety of ways. In particular, those systems comprising sources of materials set forth in Knapp et al. "Closed Loop Biochemical Analyzers" (WO 98/45481; PC/US98/06723) and Parce et al. "High Throughput Screening Assay Systems in Microscale Fluidic Devices" WO 98/00231 and, e.g., in 60/128,643 filed Apr. 4, 1999, entitled "Manipulation of Microparticles In Microfluidic Systems," by Mehta et al. are applicable.

In these systems, a "pipettor channel" (a channel in which components can be moved from a source to a microscale element such as a second channel or reservoir) is temporarily or permanently coupled to a source of material. The source can be internal or external to a microfluidic device comprising the pipettor channel. Example sources include microwell plates, membranes or other solid substrates comprising lyophilized components, wells or reservoirs in the body of the microscale device itself and others.

For example, the source of a cell type, component, or buffer can be a microwell plate external to the body structure, having, e.g., at least one well with the selected cell type or component. Alternatively, the source is a well disposed on the surface of the body structure comprising the selected cell type, component, or reagent, a reservoir disposed within the body structure comprising the selected cell type, component, mixture of components, or reagent; a container external to the body structure comprising at least one compartment comprising the selected particle type, component, or reagent, or a solid phase structure comprising the selected cell type or reagent in lyophilized or otherwise dried form.

A loading channel region is optionally fluidly coupled to a pipettor channel with a port external to the body structure. The loading channel can be coupled to an electropipettor channel with a port external to the body structure, a pressure-based pipettor channel with a port external to the body structure, a pipettor channel with a port internal to the body structure, an internal channel within the body structure fluidly coupled to a well on the surface of the body structure, an internal channel within the body structure fluidly coupled to a well within the body structure, or the like.

The integrated microfluidic system of the invention optionally includes a very wide variety of storage elements for storing reagents to be assessed. These include well plates, matrices, membranes and the like. The reagents are stored in liquids (e.g., in a well on a microtiter plate), or in lyophilized form (e.g., dried on a membrane or in a porous matrix), and can be transported to an array component, region, or channel of the microfluidic device using conventional robotics, or using an electropipettor or pressure pipettor channel fluidly coupled to a region or channel of the microfluidic system.

The above devices, systems, features, and components are used in the methods described below to modulate flow rate, make multiple concentration measurements, perform multiple assays, and reduce reagent consumption, e.g., when performing serial dilutions in a single pressure source microfluidic system.

II. Movement of Fluid Through a Microfluidic Device

In the present invention, a sample material is flowed through a main channel and various materials are added to the main channel, e.g., to dilute the sample material or to react the sample material with a reagent material. For example, in high-throughput screening applications it is sometimes useful to dilute the samples coming into the device by a factor of 10, 100, 1000, or even 10,000-fold. In vacuum driven flow systems, this can be achieved by introducing a diluting buffer into the device and designing buffer and compound fluid paths to have hydrodynamic resistances proportional to the desired dilution. However, the volumetric flow rate goes up 10-10,000-fold. Subsequent additions of reagents must then be at 10 to 10,000 times higher volumes than would be required without the dilution.

The present invention provides a flow reduction channel or bypass arm that reduces the pressure, flow rate, and/or velocity in the main channel by pulling fluid through the flow reduction channel or bypass arm. In this way the flow rate or velocity of the fluid through the device is decreased. The channels are optionally configured to decrease the flow rate so that it is substantially equal to the initial flow rate before the diluent was added or so that it is less than the initial flow rate. By reducing the flow rate, subsequent additions of reagents do not need to 10 to 10,000 times higher to meet the demands of an increased flow rate.

Typically, movement of fluidic materials through the microfluidic devices of the invention is driven by a pressure source. The pressure source is typically a vacuum source applied at the downstream terminus of the main channel. For example, in FIG. 4, vacuum source 406 is applied at one end of main channel 404. Vacuum source 406 or another type of pressure source such as those described below, applies a pressure to draw or pump fluid through the channels of the device, such as main channel 404 and flow reduction channel 408. These applied pressures, or vacuums, generate pressure differentials across the lengths of channels to drive fluid flow through them. In the interconnected channel networks described herein, such as the one shown in FIG. 4, differential flow rates on volumes are optionally accomplished by applying different pressures or vacuums at multiple ports, or preferably, by applying a single vacuum at a common waste port and configuring the various channels with appropriate resistance to yield desired flow rates. For example, the channels in FIG. 4 are configured to control flow rate through the device when vacuum source 406 is applied at the end of main channel 404. When a single vacuum source is used to draw fluid through main channel 404 and additional fluid is added through reservoir 416, the flow rate is controlled by the flow reduction channel configuration. A portion of the fluid is drawn into flow reduction channel 408, thus reducing the pressure in main channel 404.

A variety of techniques are available to apply pressure forces to microscale elements to achieve the fluid movement described above. Fluid flow (and flow of materials suspended or solubilized within the fluid, including cells or other particles) is optionally regulated by pressure based mechanisms such as those based upon fluid displacement, e.g., using a piston, pressure diaphragm, vacuum pump, probe or the like, to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, i.e., a plunger fitted into a material reservoir, for forcing material through a channel or other conduit, or is a combination of such forces.

In other embodiments, a vacuum source is applied to a reservoir or well, such as a waste well as shown in FIG. 8. Waste well 806, 806B includes a vacuum source at one end of the channel system to draw the suspension through the channel. Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

The systems of the present invention, while described in terms of a single vacuum source, may comprise other sources of fluid movement, such as electrokinetic flow and other types of pressure driven flow, including but not limited to pressure sources at multiple reservoirs or channels of the device. For example, electrokinetic techniques are optionally used to inject fluids into the device or to transfer fluids from one channel of the device to another channel in a cross-injection. The following techniques are optionally used in conjunction with those of the present invention to provide further alternatives to fluid control.

Additional methods of controlling flow in a channel or portion of the devices include the use of hydrostatic, wicking, and capillary forces to provide pressure for fluid flow of materials such as cells or sample materials. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure.

Mechanisms for focusing cells and other materials into the center of microscale flow paths, which is useful in increasing assay throughput by regularizing flow velocity, e.g., in pressure based flow, is described in "FOCUSING OF MICROPARTICLES IN MICROFLUIDIC SYSTEMS" by H. Garrett Wada et al. U.S. Ser. No. 60/134,472, filed May 17, 1999. In brief, materials are focused into the center of a channel by forcing fluid flow from opposing side channels into the main channel, or by other fluid manipulations.

In an alternate embodiment, microfluidic systems can be incorporated into centrifuge rotor devices, which are spun in a centrifuge. Fluids and particles travel through the device due to gravitational and centripetal/centrifugal pressure forces.

Another method of achieving transport through microfluidic channels is by electrokinetic material transport. "Electrokinetic material transport systems," as used herein, include systems that transport and direct materials within a microchannel and/or chamber containing structure, through the application of electrical fields to the materials, thereby causing material movement through and among the channel and/or chambers, i.e., cations will move toward a negative electrode, while anions will move toward a positive electrode. A variety of electrokinetic controllers and systems are described, e.g., in Ramsey WO 96/04547, Parce et al. WO 98/46438 and Dubrow et al., WO 98/49548, as well as a variety of other references noted herein. In the present invention electrokinetic transport or electropumping is optionally used to introduce pressure driven flow.

Pressure driven flow, as described above, is used in the present system to transport fluidic materials through the channel system to perform various assays. The flow rate in the various assays is controlled, e.g., to reduce reagent consumption and/or to modulate reaction times, by the channel configuration as described below.

III. Modulating Flow Rate Using Bypass Loops

The flow rate of a fluidic material in a microfluidic device is optionally modulated by configuring the channels such that the pressure and/or velocity or flow rate of fluid in the channels is reduced. Examples of various types of channel configurations that will reduce flow rate in microfluidic devices, e.g., in the main channels, are shown, e.g., in FIGS. 3-10, and 12.

In one embodiment, the flow reduction channel is a bypass loop, e.g., flow reduction channel 508, as shown in FIG. 5, which intersects main channel 504 in two positions. In FIG. 4, for example, flow reduction channel 408 intersects main channel 408 in a first position and a second position. The flow rate in the device in FIG. 4 is optionally modulated in the following way. A sample is sipped from sample well 402. A buffer, diluent, or other fluidic material is added to the sample from reservoir 416. As this additional fluidic material is added to the sample, the pressure increases in the main channel and the flow rate is elevated. By drawing fluid from the main channel into flow reduction channel 408, the pressure is decreased and the flow rate returns to its initial rate. The flow reduction channel is configured such that it intersects the main channel downstream from the point of introduction of the additional fluidic material. The second position of intersection for the bypass loop is typically downstream from the first position. If additional materials are to be added to the sample for reactions or assays, the second position is typically downstream of the reaction point or of the point of addition of the reagent materials. For example, in FIG. 4, flow reduction channel 408 intersects main channel 404 at a first position that is downstream of reservoir 416 and at a second position that is downstream of reagent wells 418 and 420 and upstream of pressure source 406.

Alternatively, a flow reduction channel is configured to intersect the main channel, e.g., main channel 408, upstream from the point of intersection of the additional fluidic material. In this embodiment, fluid is drawn from, e.g., main channel 408, into the flow reduction channel, thus reducing the flow rate of the fluid in the main channel prior to the addition of, e.g., a buffer, diluent, or the like. The subsequent addition, e.g., of buffer, diluent or other fluidic material, increases the flow rate, e.g., to its original or normal value, i.e., the flow rate before the fluid was drawn into the flow reduction channel. In this embodiment, the channels are configured such that the flow reduction channel is upstream from the reagent or diluent introduction channel. This way, the flow rate decreases before, e.g., the dilution mixing point, and returns to a normal value (as opposed to an elevated value) after the introduction of the diluent, buffer, or the like. This allows the mixing of the reagent or diluent into the sample to occur in a shorter distance.

In another embodiment, the flow reduction channel intersects the main channel in only one position, but is connected at its downstream end to a pressure source, typically the same pressure source that is fluidly coupled to the downstream end of the main channel. Examples of this flow reduction channel configuration include, but are not limited to, the devices of FIGS. 3 and 8. In FIG. 3, flow reduction channel 308 intersects main channel 304 and is fluidly coupled to pressure source 306. In FIG. 8, channel regions 808, 808B, 810, 810B, and 812, 812B intersect main channel region 804, 804B and are fluidly coupled to waste well 806, 806B at which a pressure source is applied.

By directing fluid through the flow reduction channels described above, the flow rate in a microfluidic device is modulated in response to the addition of material to the main channel. An added advantage of this flow rate modulation is that, in addition to maintaining a continuous or constant flow rate, subsequent reagent addition need not be in larger amounts to meet an increased flow rate demand. This saves on the amount of reagents necessary to run assays in microfluidic devices.

To further reduce reagent consumption, the reagents for assays are optionally added to secondary flow reduction channels or reaction channels. A device containing secondary flow reduction channels is illustrated in FIG. 7. For example, secondary flow reduction channels 742, 744, and 746 are fluidly coupled to flow reduction channels 712, 710, and 708 respectively. Therefore, fluid is drawn, e.g., from flow reduction channel 708 into secondary flow reduction channel 746, thus reducing the flow rate of material in channel 746. The substrates, reactants, or enzymes necessary for an assay are optionally added into the flow reduction channels or into the secondary flow reduction channels. For example, reagents are optionally added from reservoir 726 or 728 into reaction channel 742. If reaction channel 742 has a smaller cross-sectional dimension than flow reduction channel 712, then reagent consumption is additionally reduced due to the smaller dimension of the reaction channel. Alternatively, they are added into the main channel after a portion of the fluid has been drawn off into a flow reduction channel. In either case, the amount of reagent material that must be added to conduct an assay is diminished, due to decreased flow rate and/or decreased channel dimensions.

IV. Obtaining Multiple Concentration Measurements and Performing Multiple Assays in a Microfluidic Device Another added benefit to using flow reduction channels in a microfluidic device is that the channels are optionally used to obtain multiple measurements on the same sample material in one assay. For example, a diluent is optionally added to create a 10:1 dilution of a sample material in the main channel. When a portion of the 10:1 diluted material is drawn from the main channel into a flow reduction channel, a measurement is optionally obtained in a detection region positioned within the flow reduction channel. For every additional dilution level obtained in this manner, e.g., 100:1, 1000:1, or 10,000:1, a separate detection region is optionally placed within the flow reduction channel and a signal detected.

For example, see FIG. 6. A detector is placed proximal to each flow reduction channel, e.g., 608, 610, and 612. Additionally, a detector is placed proximal to the main channel. Typically, when an assay is performed in the device, the detection region where the detector is placed is positioned downstream of the reagent reservoirs, e.g., reservoirs 626, 628, 622, and 624. Then the assay is run and the detector is used to detect a signal that is correlated with the assay results.

In another embodiment, a movable detector is used and is moved between detection regions such that a signal is detected from each of the detection regions of interest.

Alternatively, a single detector is positioned in such a way that it detects a signal from all the flow reduction channels concurrently. Such a configuration is shown in FIG. 8. The main channel and flow reduction channels comprise parallel channel regions 804, 804B, 808, 808B, 810, 810B, and 812, 812B, which converge in a single detection window 832, 832B.

Using these channel configurations, it is possible to take measurements on a single sample at multiple concentrations using one assay. In addition, because the reagent reservoirs are optionally positioned such that they are fluidly coupled to the flow reduction channels, reaction or assays are optionally performed at the various dilution levels obtained from the serial dilution. For example, as shown in FIG. 6, reservoirs 622 and 624 are fluidly coupled to flow reduction channels 608 and 610. Therefore reactions or assays are optionally performed in flow reduction channels 608 and 610 which contain different concentrations of sample when operated as described above for serial dilutions.

The channel configurations described herein are optionally used, e.g., to perform multiple assays or measure multiple samples, e.g., concurrently. A single sample or test compound is optionally introduced into a microfluidic device, e.g., through a capillary fluidly coupled to the device. The test compound is optionally a drug, a potential drug, a chemical compound, an enzyme, a protein, a nucleic acid, or the like. The sample is optionally divided into n portions, n ranging from about 2 to about 100. The portions are optionally used at their initial concentration or diluted as described above.

Each portion is flowed through one of x assay channels, e.g., parallel assay channels, x ranging from about 1 to about 100. As used herein, "assay channel" refers to a microscale channel, e.g., in a parallel configuration, that is used for performing assays, tests, screens, or the like, e.g., biochemical assays, on a variety of compounds, e.g., chemical or biochemical compounds. The flow reduction channels of the present invention are optionally used as assay channels. Portions of the sample or test compound are optionally flowed into the assay channels simultaneously to perform multiple simultaneous assays.

Once the sample portions are flowed into an assay channel, one or more reagents are added to each channel, thereby combining the reagents and the sample portions and performing an assay. A different reagent is optionally added to each channel, thereby performing y different assays in the x assay channels, y being between about 1 and about 100. The assays are optionally performed simultaneously, e.g., the various sample portions are concurrently flowed through the channels and concurrently reacted with one or more reagents, e.g., different reagents. The reagents are optionally used to perform HSA binding assays, target screens, drug screens, enzyme assays, fluorescence assays, dose-response assays, selectivity screens, protease assays, binding assays, and the like. An alternate method of performing different assays or subjecting a single compound to multiple chemistries comprises using different channel chemistries in each of the assay channels.

Each assay results in z products, z ranging from about 1 to about 1000. For example, each reaction produces one or more products, the products in each of the x channels from y assays are optionally simultaneously detected as they flow through a detection region, e.g., a detection region that is proximal to all x channels. In this manner, multiple assays are performed simultaneously on a single test compound using the devices and the methods of the present invention.
V. Assays that are optionally performed using the devices of the invention.

A device, such as the one in FIG. 8, is optionally used to test compounds for inhibition of a target enzyme in a continuous-flow enzyme inhibition assay. A device, such as that in FIG. 8, incorporates a capillary attached to the microfluidic body structure at capillary attachment point 802, 802B to serve as a sample injection port, and four parallel reaction/processing channels, e.g., channel regions 804, 804B, 808, 808B, 810, 810B, and 812, 812B. The channel regions incorporate one or more fixed-dilution stages that vary the final concentration of the test compound over a three order of magnitude range. In addition, the four parallel channel regions comprise an assay region, in which the compounds are mixed with enzyme and substrate, and detection window 832, 832B, in which the four channel regions 804, 804B, 808, 808B, 810, 810B, and 812, 812B are brought into close proximity to facilitate simultaneous monitoring of the resultant fluorescence using imaging or scanning techniques.

Test compounds are injected into the microfluidic device via a sample capillary by applying a vacuum at waste well 806, 806B. In channel region 804, 804B, the main channel region, the test compound is brought into the device and mixed with enzyme and substrate without further dilution. Channel region 808, 810B incorporates one dilution stage to accomplish a 10-fold reduction in concentration by adding additional assay buffer from reservoir 816, 816B and allowing the components to mix and drawing off additional fluid into a waste channel to keep the overall flow rate constant. Similarly, channel region 810, 810B and 812, 812B incorporate two and three dilution stages respectively to accomplish 100-fold and 1000-fold reductions in concentration of the test compound. By keeping the waste streams from the dilution stages separate instead of connected as shown in the figure, the test compounds are optionally monitored for autofluorescence (because the waste channels are also imaged or scanned) and this data is optionally used to correct raw fluorescence data for the assay before calculation of % inhibition.

To further modulate the flow rate, the channel dimensions are optionally adjusted, e.g., by incorporating loops and serpentine features, varying widths, depths, to vary relative hydrodynamic resistances in such a way that the desired dilution factors, flow rates, and mixing times are achieved. The sample injection circuit is optionally adjusted in such a way that the test compound solution reaches the parallel channel regions simultaneously. Similarly, the overall length of the parallel channel regions (and waste streams if desired) are optionally adjusted so that the samples reach the detection window in synchronized fashion. Similar designs are optionally used in kinase assays, binding assays, cell-based assays, etc.

Alternatively, the devices of the invention are used to concurrently perform multiple assays. For example, an HSA assay and a high throughput target screen are optionally performed in combination, e.g., on a single sample plug divided into portions that are flowed into the various assay channels of the invention, each undergoing a different reaction chemistry. Alternatively, intrinsic drug fluorescence is measured in combination with a high throughput target screen or a panel of similar enzymes is concurrently evaluated in a selectivity screen. In other embodiments, a dose-response experiment is performed using in-line dilutions as described above, to study a whole range of dissociation constants with a single sample.

In another embodiment, the same reaction is performed in each channel, the only difference being, e.g., a different enzyme isoform. For example, single nucleotide polymorphisms (SNP) are currently known and quickly being determined for all enzymes, i.e., gene products. The enzymes are optionally drug targets, enzymes important in metabolism, or the like, e.g., P450 enzymes. The enzymes are typically screened against potential drugs or drug compounds, e.g., in a high throughput format. Performing a screen in parallel versus multiple forms of an enzyme is typically probative with respect to reagent consumption and time. Differences in individual enzymes, e.g., p450 enzymes, can be an important factor impacting differential drug-drug interactions and side-effects of drugs. The devices of the present invention are optionally used to simultaneously screen all desired forms of an enzyme or protein in parallel using one sample. This allows, e.g., consideration of key SNP differences between individual compounds early in the drug discovery process, e.g., before costly ensuing phases including clinical trials with human subjects. In addition such methods are useful in high-throughput target screening and in non-target dependent high throughput screening.

Different reactions are performed concurrently in the same device, e.g., by the incorporation of multiple reagent wells to add different reagents to each channel as described above. For example, reservoir 822 optionally adds reagents to channel region 804, reservoir 820 to channel 808, reservoir 826 to channel 810 and reservoir 824 to channel 812. Channels 842, 844, and 846 are optional since multiple reactions are optionally performed in a device without the flow reduction channels. Alternatively, the flow reduction channels are used as additional assay channels or to dilute the sample portions before subjecting them to the various assays.

In other embodiments, multiple assays are concurrently carried out in a single device with a single sample or test compound by altering channel chemistries of the various assay channels of the device, e.g., by using different channel coatings, materials, and the like, in the different assay channels. For example, one channel optionally contains a separation matrix or optionally comprises functionalized glass, e.g., silanized glass. In some embodiments, different reagents, beads comprising different reagents, or the like are pre-loaded into the channels to provide different chemistries. Surface modification of polymeric substrates may take on a variety of different forms, including coating with an appropriately charged material, derivatizing molecules present on the surface to yield charged groups on that surface, and/or coupling charged compounds to the surface. For descriptions regarding application and use of channel coatings, see, e.g., U.S. Pat. No. 5,885,470, by Parce et al., entitled "Controlled Fluid Transport in Microfabricated Polymeric Substrates" and published PCT application WO 98/46438 of the same name.

VI. Suppression of Pressure Perturbations due to Spontaneous Injection into a Microfluidic Device.

Spontaneous injection typically occurs in microfluidic systems utilizing an external capillary, e.g., to transport samples from a sample plate into the microfluidic device. As used herein, the phrase "spontaneous injection" refers to the action of fluid or other material to move into a given passage or conduit under no externally applied forces, e.g., applied pressure differentials, applied electric fields, etc. Typically, and as used herein, spontaneous injection refers to the action of fluids at the tip of a fluid-filled capillary channel in moving into the channel as a result of capillary action within the channel, surface tension on the fluid outside the channel, or the like. Thus, a fluid or other material that is "spontaneously injected" into a channel, chamber or other conduit, moves into that channel, chamber or other conduit without the assistance of an externally applied motive force.

The phenomenon of spontaneous injection is generally viewed as a problem in capillary electrophoresis applications as it presents a constant volume error in sampling (independent of sampled volume) that can vary depending upon the geometry of the capillary channel and channel tip. Methods for reducing or eliminating this effect are provided in, e.g., U.S. Ser. No. 09/416,288, "External Material Accession Systems" by Chow et al., which also provides methods for exploiting this phenomenon to provide improved sample accession, e.g., sampling extremely small volumes of fluid.

Spontaneous injection into a microfluidic device comprising an external sipper capillary is also known to induce a perturbation in flow rate under a substantially constant driving force, such as pressure, e.g., a single vacuum source, or electrokinetically driven flow. As a sipper capillary is lifted out of a fluid reservoir, e.g., a sample well, the curvature of the drop of liquid at the end of the capillary exerts an additional pressure inward into the capillary, resulting in a higher flow rate. The perturbation in flow rate results in a perturbation in assay signal, which can interfere with quantitative analysis of the assay results. See, e.g., FIG. 11. For example, the perturbation in signal can obscure an inhibition in an enzymatic inhibition reaction. Therefore, it is desirable to minimize the pressure perturbations due to increased flow rate when a drop of fluid is spontaneously injected into a microfluidic device.

The present invention provides methods for suppressing the pressure perturbations due to spontaneous injection into a microfluidic device. The methods typically comprise dipping an open end of a capillary into a sample source, e.g., a microwell plate, thereby drawing a sample from the sample source into the capillary. The capillary is typically an external sipper capillary fluidly coupled to a microfluidic device. The method comprises withdrawing the open end of the capillary from the sample source. A first portion of the sample remains on the open end and is spontaneously injected into the capillary due to surface tension exerting pressure on the capillary. A second portion of the sample is flowed from the capillary into a main channel, which intersects the capillary at a first intersection point or pressure node. A third portion of the sample is flowed through a shunt channel to create a pressure differential between the first intersection point or pressure node and the open end of the capillary. The shunt channel typically intersects the main channel at the first intersection point or downstream of the first intersection point. The flow of fluid through the shunt or by-pass channel changes the pressure at the first intersection point, thereby suppressing pressure perturbations in the main channel. The pressure at the first intersection point is optionally greater than or less than the pressure at the open end of the capillary, which is typically atmospheric pressure.

The above method reduces the effect of spontaneous injection by flowing fluid from the sipper capillary into a by-pass channel to change the pressure points in the system. For example, the pressure node at which an-on-chip reagent is mixed with or joins the reagent or sample introduced into the microfluidic device from a sipper capillary determines the extent of pressure perturbation in the microfluidic device. Typically, the further away from atmospheric pressure this pressure node is the smaller the spontaneous injection pressure perturbation effect. The flow reduction channels or shunt channels of the present invention are used to shape the pressure at this pressure node or intersection point and minimize the pressure perturbation. In addition, the shunt channel is optionally a controllable channel in which the pressure is optionally adjusted to increase or decrease the pressure differential. For example, a pressure source, e.g., coupled to a controller, is optionally fluidly coupled to a shunt channel to control the pressure in the shunt channel, e.g., by applying a positive or negative pressure to the shunt channel. Alternatively, the shunt channel is configured to provide a particular pressure differential, e.g., using width, depth, channel coatings or the like.

For example, in a microfluidic device without a shunt channel, such as that shown in FIG. 9A, the internal pressure node $P_1$ is determined by the flow rate $Q_1$, the hydrodynamic resistance $R_1$ and the applied pressure $P_0$ as follows:

$$P_1 = P_0 + Q_1 R_1$$

Figure 9B:
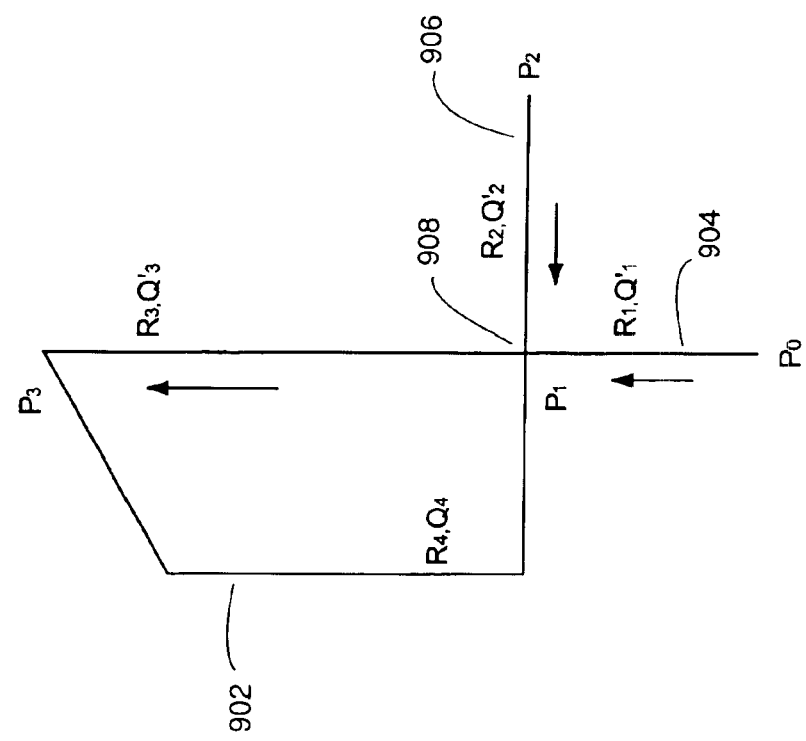
FIG. 9: Panel A provides a schematic of a microfluidic device without a shunt channel and Panel B provides a schematic of a microfluidic device comprising a shunt channel. Both devices comprise a sipper capillary.
Figure 9A:
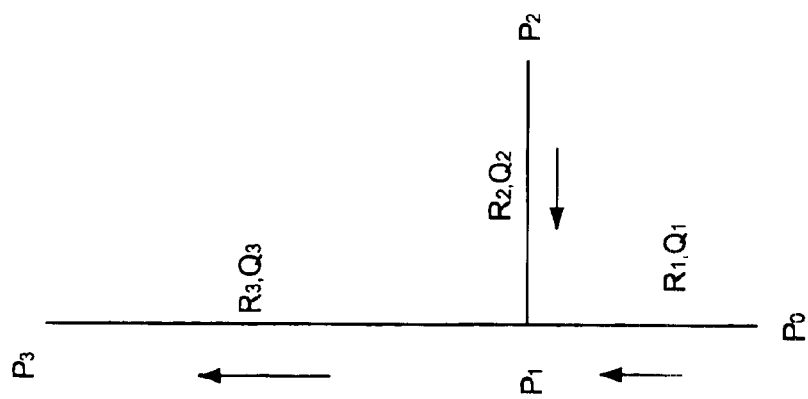

FIG. 9B shows a device with shunt channel 902 added. As fluid is flowed into shunt channel 902, e.g., from capillary 904, $Q_1'$ is increased to $Q_1'$, e.g., when all external pressure nodes, $P_0$, $P_2$, and $P_3$ are unchanged. The internal pressure node $P_1$, at the intersection of capillary 904, shunt 902, and side channel 906 is as follows:

$$P_1' = P_0 + Q_1' R_1$$

Since $Q_1'$ is greater then $Q_1$, $P_1'$ is also greater then $P_1$. This pressure difference makes the device of FIG. 9B more resistant to spontaneous injection pressure perturbations at $P_0$, e.g., intersection point 908, than the device of FIG. 9A. Other benefits of the shunt design include, but are not limited to, a reduced level of relative hydrodynamic dispersion of the sample plugs through the capillary and a reduced tailing of the sample plugs through the sipper joint, connecting the capillary to the microchannel on the device.

VII. Instrumentation

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquotting, and the like. Similarly, downstream operations may include similar operations, including, e.g., separation of sample components, labeling of components, assays and detection operations, electrokinetic or pressure-based injection of components into contact with particle sets, or materials released from particle sets, or the like.

In the present invention, materials such as cells, proteins, antibodies, enzymes, substrates, buffers, or the like are optionally monitored and/or detected, e.g., so that presence of a component of interest can be detected, an activity of a compound can be determined, or an effect of a modulator on, e.g., an enzyme's activity, can be measured. Depending on the label signal measurements, decisions are optionally made regarding subsequent fluidic operations, e.g., whether to assay a particular component in detail to determine, e.g., kinetic information.

The systems described herein generally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Fluid Direction System

A variety of controlling instrumentation is optionally utilized in conjunction with the microfluidic devices described above, for controlling the transport and direction of fluidic materials and/or materials within the devices of the present invention, e.g., by pressure-based or electrokinetic control.

In the present system, the fluid direction system controls the transport, flow and/or movement of a sample through the microfluidic device. For example, the fluid direction system optionally directs the movement of a sample into and through the main channel, where the sample is optionally diluted with a buffer or other diluent. It optionally directs movement of the buffer or other diluent from the source of the material into the main channel, resulting in a first diluted sample. It also directs movement of a portion of the first diluted sample into a flow reduction channel, while a second portion of the first diluted sample remains flowing through the main channel. The fluid direction system also optionally directs the movement of a second aliquot of buffer into the main channel to perform a serial dilution, thus creating a second diluted sample. Thereafter, the fluid direction system would direct a first portion of the second diluted material into a second flow reduction channel, while the second portion of the second diluted material remains in the main channel. The fluid direction system also may iteratively repeat these movements to create more serial dilutions of the sample material, reducing the pressure in the main channel after each dilution by directing a portion of the fluidic materials into a flow reduction channel.

After the desired dilution levels are obtained in the various channels of the system, the fluid direction system optionally directs the movement of one or more reagent materials, e.g., substrates, enzymes, and the like, from reagent reservoirs into the main channel and/or flow reduction channels to react with the sample materials and/or diluted materials. To decrease reagent usage the fluid direction system optionally directs movement of the diluted samples from the flow reduction channels into secondary flow reduction channels or reaction channels. In addition, movement of the sample material and diluted materials through the channels and into the detection region, where they are detected, is also controlled by the fluid direction system.

To perform multiple assays, e.g., on a single sample, the fluid direction system divides a sample into n portions and directs the n sample portions into x assay channels, e.g., parallel assays channels such as those in FIGS. 8A and 8B. The fluid direction system also optionally directs the addition of various reagents to each of the x channels. Different reagents are optionally added to each of the x channels, thereby exposing each portion of the sample to a different chemistry, e.g., to a different reaction or assay, thereby performing y different assays and producing z different products. The number of sample portions used, n, is typically between about 2 and about 100. Typically the number of sample portions is substantially equal to the number of channels, x. The fluid direction system typically directs one sample portion into each different channel. Alternatively, a device with 10 channels is used and the sample is only divided in 2 portions such that only 2 channels are used. In other embodiments, a different sample is directed into each of the 10 channels. The number of channels is typically between about 2 and about 100. Preferably, the number of channels ranges from about 2 to about 20. More preferably, the number of channels is from about 4 to about 10 channels. Once the samples are in the channels, the fluid direction system directs various reagents from the reservoirs into the assay channels, e.g., to perform y different assays. The number of different assays, y, is typically between about 2 and about 100. However, the number of assays does not have to equal the number of channels or the number of sample portions. A different assay is optionally performed in each one of the x channels. For example, a number of different enzyme substrates are optionally screened simultaneously in the different channels of the invention or a number of different protein binding sites are optionally probed simultaneously by testing each binding site in a different channel. Alternatively, one assay, e.g., site I HSA binding, is performed in some channels, e.g., half of the channels, and another assay, e.g., site II HSA binding, is performed in the remaining channels. The y assays typically produce z different products, e.g., each assay produces one or more products. Therefore, the number of products is typically at least equal to the number of assays, but is often greater than the number of assays, y. The number of products typically ranges from about 1 to about 10,000, more typically from about 2 to about 1000 and most typically from about 2 to about 100. Each assay typically results in one or more products, which the fluid direction system directs through the assay channels and into a detection region for detection, e.g., concurrent detection, e.g., fluorescent detection, from assay channels that converge into a single detection region.

To suppress pressure perturbations created by spontaneous injection of a fluid from an external capillary into a microfluidic device, the fluid direction system, which comprises at least one fluid control element fluidly coupled to a main channel, to a shunt channel, and to a capillary, directs movement of a sample from a first sample source into an inlet region of the capillary and movement of the sample from the inlet region of the capillary to an outlet region of the capillary. The sample is then directed from the outlet region of the capillary into the upstream region of a main channel. A first portion of the sample from the upstream region of the main channel is flowed into a shunt channel, as described above, and a second portion of the sample remains in the main channel. This fluid movement maintains the intersection of the main channel and the capillary at a pressure that is different from the pressure at the inlet region of the capillary. The difference in pressure reduces the effect of the spontaneous injection pressure perturbations.

Fluid transport and direction in microfluidic devices, e.g., as described above, are typically controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. As noted above, the systems described herein can also utilize electrokinetic material direction and transport systems. Preferably, external pressure sources are used, and applied to ports at channel termini. More preferably, a single pressure source is used at a main channel terminus. Typically, the pressure source is a vacuum source applied at the downstream terminus of the main channel. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Ser. No. 09/238,467, filed Jan. 28, 1999.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also optionally used to provide for electrokinetic injection or withdrawal of material downstream of the region of interest to control an upstream flow rate. The same instrumentation and techniques described above are also utilized to inject a fluid into a downstream port to function as a flow control element.

Detector

The devices herein optionally include signal detectors, e.g., which detect fluorescence, phosphorescence, radioactivity, pH, charge, absorbance, luminescence, temperature, magnetism, color, or the like. Fluorescent and chemiluminescent detection are especially preferred.

The detector(s) optionally monitors one or a plurality of signals from the one or more detection regions of the device, e.g., detection regions 332 or 832, 832B in FIGS. 3 and 8. The one or more detection regions may correspond to the various sample concentrations achieved by the serial dilutions or to the various samples being assayed. For example, the detector optionally monitors an optical signal that corresponds to a labeled component, such as a labeled antibody or protein located, e.g., in detection region 832, 832B.

In one embodiment, the detection region spans multiple main channels and/or flow reduction channels and one detector is used to detect signal from all channels concurrently. In FIG. 8, for example, detection region 832, 832B monitors signals from main channel region 804, 804B, which contains, e.g., an undiluted sample, and parallel regions 808, 808B, 810, 810B, and 812, 812B, which contain e.g., a 1:10 dilution of the sample material, a 1:100 dilution of the sample material, and a 1:1000 dilution of the sample material. Alternatively, a single detector proximal to each of 2 or more assay channels, e.g., parallel assay channel regions, detects the results of the two or more different assays, e.g., performed on the same sample which has been divided into the 2 or more channels to undergo multiple assays. The results of a plurality of enzyme assays, e.g., producing different products, are optionally detected simultaneously by a detector placed proximal to all relevant assays channels. For example, the results of HSA binding to site I and site II are optionally detected concurrently when simultaneously probed in two different channels.

Alternatively, if the flow reduction channels are not proximal to one another, a separate detector is optionally used to detect the signal from each channel. For example, in FIG. 6 the channels are optionally configured so that the detectors are not proximal to one another. If the channels loop around to make the detectors proximal to each other, then a single detector would suffice. When a single detector does not detect all the signals or when different types of detection are required the channel configuration of FIG. 6 is optionally used. Detectors are placed proximal to detection region 632 to detect a signal from main channel 604, detection region 634 to detect a signal from flow reduction channel 612, detection region 636 to detect a signal from flow reduction channel 610, and detection region 638 to detect a signal from flow reduction channel 608. Alternatively, a single detector is moved between detection regions 632, 634, 636, and 638.

In the above case detection optionally works as follows: an undiluted, unreacted sample is detected in detection region 632, an undiluted reacted sample in detection region 634, a twice diluted reacted sample in detection region 636, and a sample that has been diluted once and reacted with the reagents in detection region 638. Once detected, the flow rate and velocity of cells in the channels is also optionally measured and controlled as described above.

Examples of detection systems useful in the present invention include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "proximal," to a particular element or region, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. Example detectors include photo multiplier tubes, a CCD array, a scanning detector, a galvo-scanner or the like. For example, in preferred aspects, a fluorescence, chemiluminescence or other optical detector is used in the assay. Proteins, antibodies, or other components which emit a detectable signal can be flowed past the detector, or, alternatively, the detector can move relative to an array to determine protein position (or, the detector can simultaneously monitor a number of spatial positions corresponding to channel regions, e.g., as in a CCD array).

In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials such as labeled cells, the detector typically includes a light source which produces light at an appropriate wavelength for activating the fluorescent material, as well as optics for directing the light source through the detection window to the material contained in the channel or chamber. The light source can be any number of light sources that provides an appropriate wavelength, including lasers, laser diodes and LEDs. Other light sources are required for other detection systems. For example, broad band light sources are typically used in light scattering/transmissivity detection schemes, and the like. Typically, light selection parameters are well known to those of skill in the art.

The detector can exist as a separate unit, but is preferably integrated with the controller system, into a single instrument. Integration of these functions into a single unit facilitates connection of these instruments with a computer (described below), by permitting the use of few or a single communication port(s) for transmitting information between the controller, the detector and the computer. Integration of the detection system with a computer system typically includes software for converting detector signal information into assay result information, e.g., concentration of a substrate, concentration of a product, presence of a compound of interest, or the like.

Computer

As noted above, either or both of the fluid direction system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. For example, the software optionally directs the fluid direction system to transport the sample to the main channel, the buffer or other diluent to the main channel, a portion of the sample or diluted sample to a flow reduction channel, a portion of the sample or diluted material through the main channel, a portion of a sample or diluted material into a secondary flow reduction channel, a reagent material into the main channel, a flow reduction channel or a secondary flow reduction channel, and any other movement necessary to perform the assay of interest and/or detect a component of interest.

The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring of materials in the channels. Additionally the software is optionally used to control electrokinetic or pressure-modulated injection or withdrawal of material. The injection or withdrawal is used to modulate the flow rate as described above.

In addition, the computer optionally includes software for deconvolution of the signal or signals from the detection system. For example, the deconvolution distinguishes between two detectably different spectral characteristics that were both detected, e.g., when a substrate and product comprise detectably different labels.

EXAMPLE INTEGRATED SYSTEM

Figure 2:
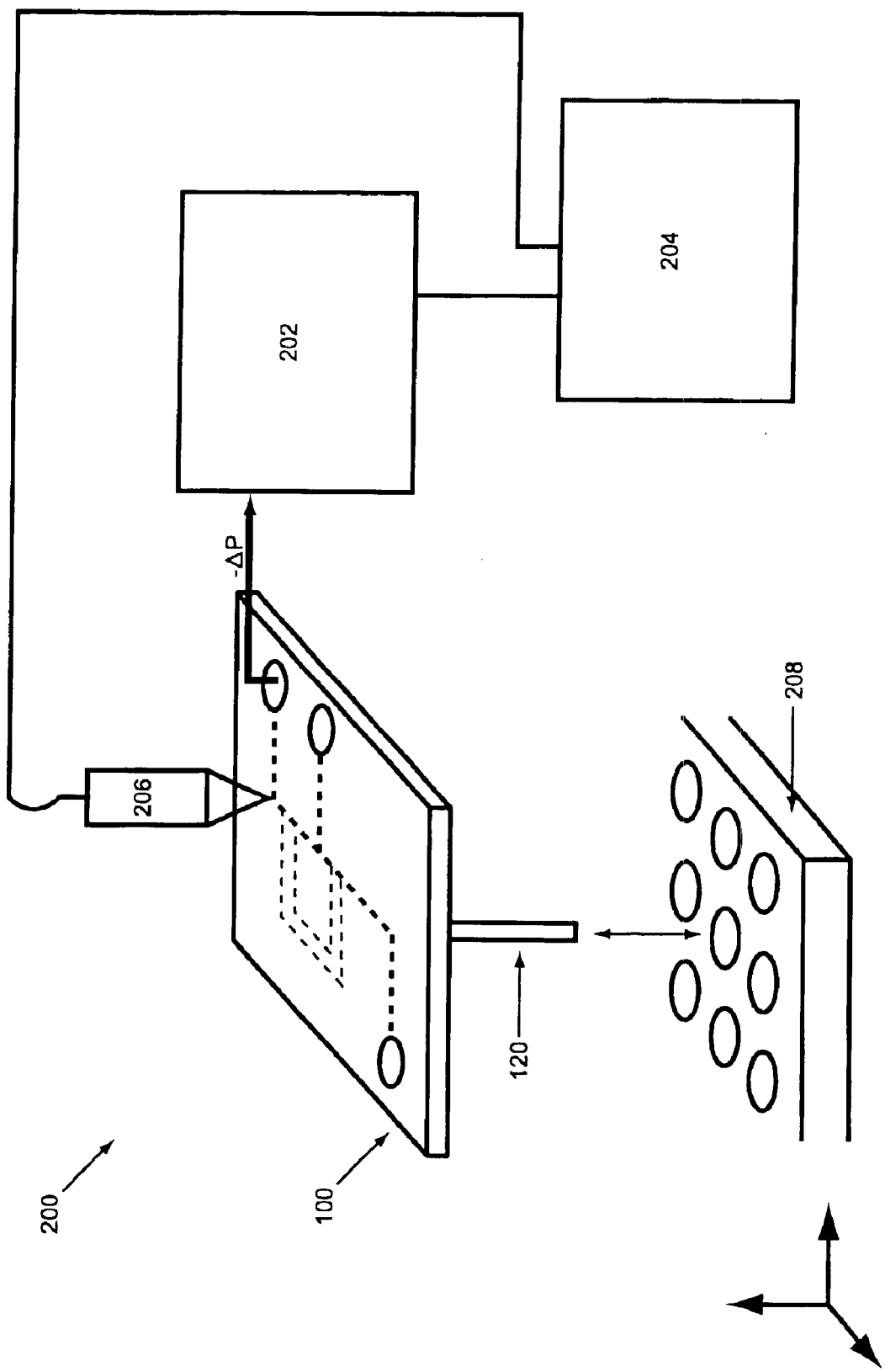
FIG. 2: Schematic drawing of an integrated system of the invention further depicting incorporation of a microwell plate, a computer, detector, and a fluid direction system. The integrated system is optionally used with either the device or body structure of FIGS. 3, 4, 5, 6, 7, 8, 9, 10, or 12, or any other suitable microfluidic device.

FIG. 1, Panels A, B, and C and FIG. 2 provide additional details regarding example integrated systems that are optionally used to practice the methods herein. As shown, body structure 102 has main channel 104 disposed therein. A sample or mixture of components is optionally flowed from pipettor channel 120 towards reservoir 114, e.g., by applying a vacuum at reservoir 114 (or another point in the system) or by applying appropriate voltage gradients. Alternatively, a vacuum is applied at reservoirs 108, 112 or through pipettor channel 120. Additional materials, such as buffer solutions, substrate solutions, enzyme solutions, and the like, as described above are optionally flowed from wells 108 or 112 and into main channel 104. Flow from these wells is optionally performed by modulating fluid pressure, or by electrokinetic approaches as described (or both). As fluid is added to main channel 104, e.g., from reservoir 108, the flow rate increases. The flow rate is optionally reduced by flowing a portion of the fluid from main channel 104 into flow reduction channel 106 or 110. The arrangement of channels depicted in FIG. 1 is only one possible arrangement out of many which are appropriate and available for use in the present invention. Alternatives are provided in FIGS. 3, 4, 5, 6, 7, 8, 9, 10 and 12. Additional alternatives can be devised, e.g., by combining the microfluidic elements described herein, e.g., flow reduction channels, with other microfluidic devices described in the patents and applications referenced herein. Furthermore the elements of FIGS. 3, 4, 5, 6, 7, 8, 9, 10 and/or 12 are optionally recombined to provide alternative configurations.

Samples and materials are optionally flowed from the enumerated wells or from a source external to the body structure. As depicted, the integrated system optionally includes pipettor channel 120, e.g., protruding from body 102, for accessing a source of materials external to the microfluidic system. Typically, the external source is a microtiter dish or other convenient storage medium. For example, as depicted in FIG. 2, pipettor channel 120 can access microwell plate 108, which includes sample materials, buffers, substrate solutions, enzyme solutions, and the like, in the wells of the plate.

Detector 206 is in sensory communication with channel 104, detecting signals resulting, e.g., from labeled materials flowing through the detection region. Detector 206 is optionally coupled to any of the channels or regions of the device where detection is desired. Detector 206 is operably linked to computer 204, which digitizes, stores, and manipulates signal information detected by detector 206, e.g., using any of the instructions described above, e.g., or any other instruction set, e.g., for determining concentration, molecular weight or identity, or the like.

Fluid direction system 202 controls voltage, pressure, or both, e.g., at the wells of the systems or through the channels of the system, or at vacuum couplings fluidly coupled to channel 104 or other channel described above. Optionally, as depicted, computer 204 controls fluid direction system 202. In one set of embodiments, computer 204 uses signal information to select further parameters for the microfluidic system. For example, upon detecting the presence of a component of interest in a sample from microwell plate 208, the computer optionally directs addition of a potential modulator of component of interest into the system.

Kits

Generally, the microfluidic devices described herein are optionally packaged to include reagents for performing the device's preferred function. For example, the kits can include any of microfluidic devices described along with assay components, reagents, sample materials, proteins, antibodies, enzymes, substrates, control materials, or the like. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one embodiment, the device itself comprises a pipettor element, such as an electropipettor for introducing material into channels and chambers within the device). In the former case, such kits typically include a microfluidic device with necessary reagents predisposed in the channels/chambers of the device.

Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

Kits also optionally include packaging materials or containers for holding microfluidic device, system or reagent elements.

The discussion above is generally applicable to the aspects and embodiments of the invention described in the claims.

Moreover, modifications can be made to the method and apparatus described herein without departing from the spirit and scope of the invention as claimed, and the invention can be put to a number of different uses including the following:

The use of a microfluidic system for performing the assays set forth herein.

The use of a microfluidic system for obtaining measurements at multiple concentrations as described herein.

The use of a microfluidic system for performing an assay at multiple concentrations as described herein.

The use of a microfluidic device for performing multiple assays as described herein.

The use of a microfluidic device for performing concurrent multiple assays on a single test compound as described herein.

The use of a microfluidic system for reducing reagent consumption as described herein.

The use of a microfluidic system as described herein for performing serial dilutions of a sample.

The use of a microfluidic system or device for controlling or modulating flow rate as described herein.

The use of a microfluidic system or device for suppressing pressure perturbations due to spontaneous injection as described herein.

An assay utilizing a use of any one of the microfluidic systems or substrates described herein.

VIII. EXAMPLES

Example 1

Phosphatase Assays

A microfluidic device comprising the channel layout shown in FIG. 8B was used to obtain data in a phosphatase assay. In a typical assay, approximately 60 microliters of enzyme solution are loaded into wells 820b and 824b. Substrate is added into wells 822b and 826b and wells 816b and 818b are loaded with buffer. The final concentration of reagents delivered to the main reaction channel is determined by the relative flow rates in the side channels and the reaction channels. Reaction times on the chip are varied either by moving the detection point to different locations along the reaction channels or by varying the negative pressure applied at waste well 806b.

Reagents

Inhibitors, e.g., commercially available phosphatase inhibitors, at various concentrations are loaded into a microtiter plate for loading into the device through a sipper capillary attached at capillary attachment point 802b. For example, typical inhibitor concentrations include: 1 mM, 0.625 mM, 1.25 mM, 2.5 mM, 5 mM, and 10 mM.

A typical buffer used for phosphatase reactions comprises 25 mM Tris-HCl, pH 7.0, 50 mM NaCl, 2 mM EDTA, 0.01% Brij 35, 5 mM DTT, and 500 NDSB.

For enzymes, a 1:100 dilution of phosphatase is prepared (approximately 100 nm) is typically placed in the well of the microfluidic device.

A 100 μM phosphatase substrate solution is placed in substrate wells.

A 1 nM solution of marker dye Cy5 from Beckman is placed in the microtiter plate along with the inhibitor samples.

Enzyme Inhibition and $K_i$ Determination

Inhibitor titration experiments were carried out using a competitive peptide phosphatase inhibitor with high affinity for the phosphatase being assayed. The peptide concentrations typically range from 0.625 to 10 mM in the microplate. Percent inhibition values were calculated from the decrease in fluorescence corresponding to the inhibitor injection, the enzyme+substrate baseline, and the measured substrate-only background. Analysis of this data (with the 10 highest inhibitor concentrations from 100% and 10% channel excluded from the analysis because they gave near-saturating responses) yielded a $K_i$ value of 169.55 μM when analyzed using a Dixon plot. From the plot of inhibitor concentration versus percent inhibition, the $IC_{50}$ value of 160 and 200 μM were estimated when using substrate concentration of 100 μM and 50 μM in the substrate well of the device, and the $K_i$ value of 113 μM and 109 μM were calculated using the following equation:

$$IC_{50}=K_i*(1+[S]/K_m)$$

Figure 15:
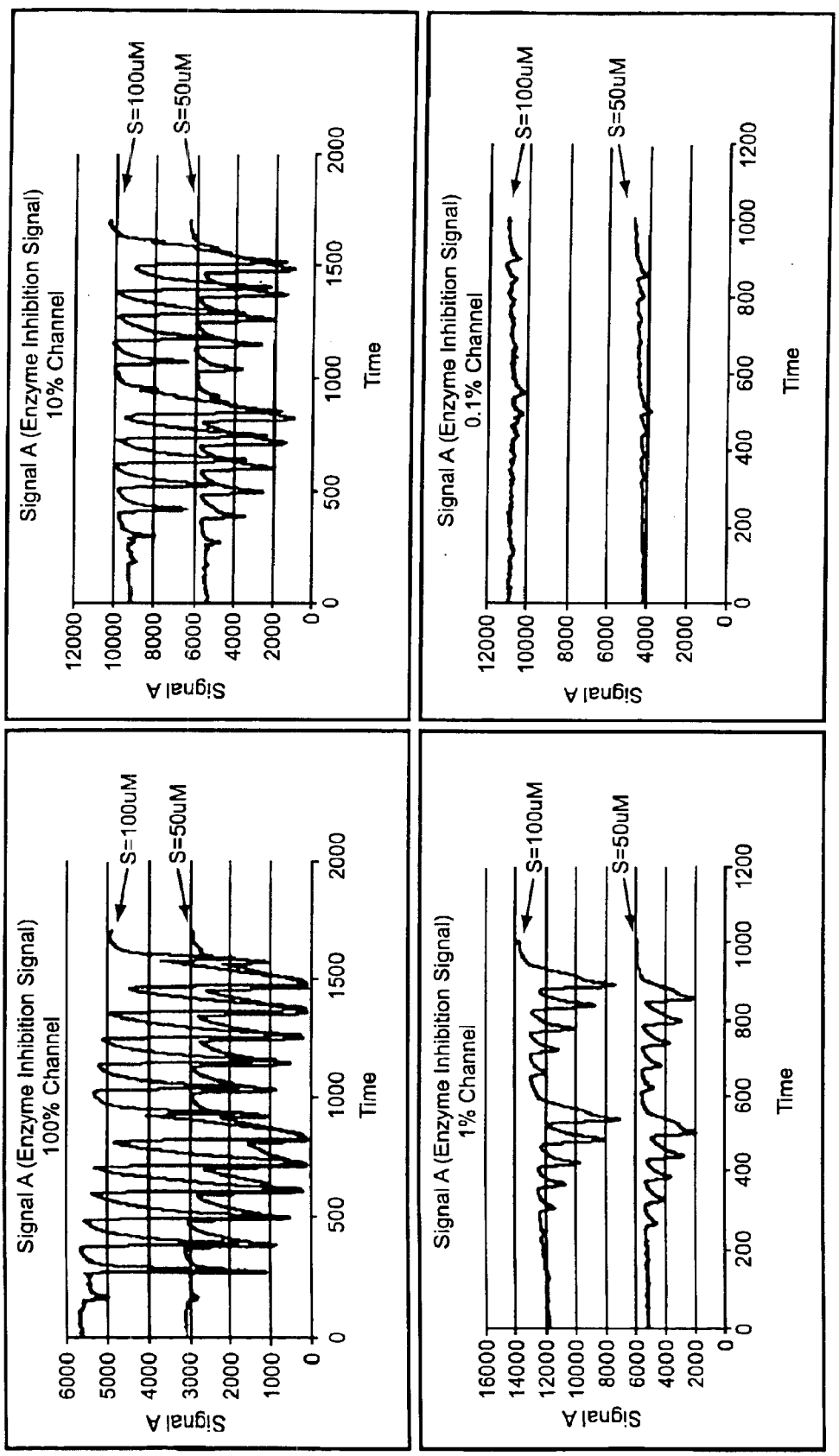
FIG. 15: Inhibitor titration measured using a device as shown in FIG. 8B using two substrate concentrations.
Figure 16:
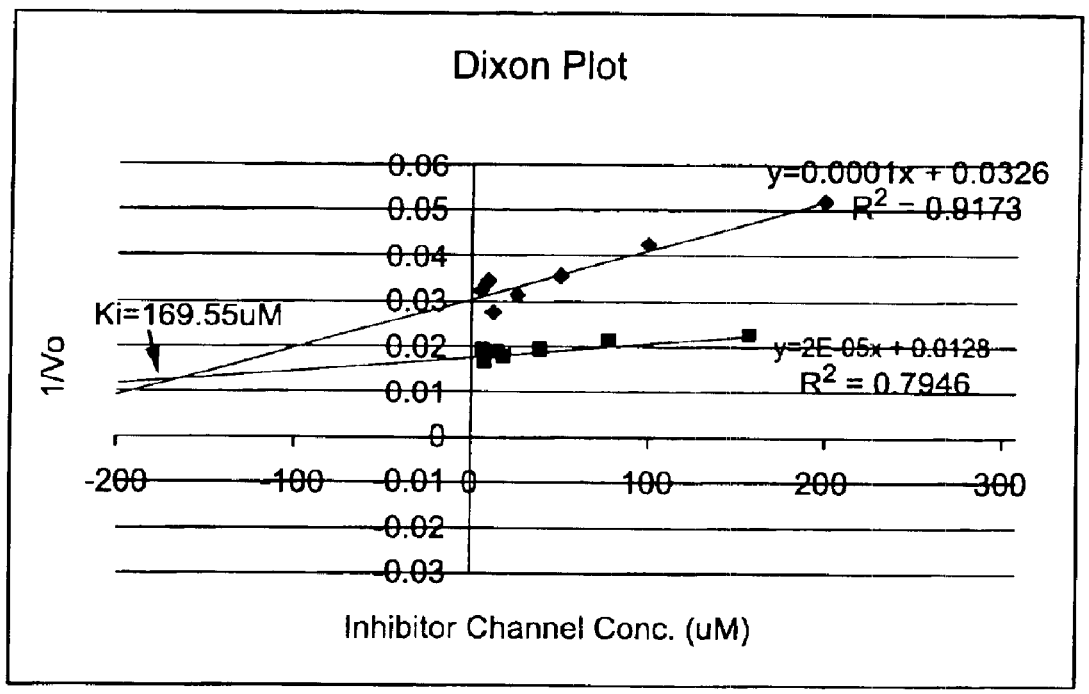
FIG. 16: $K_i$ determined by a Dixon plot.
Figure 17:
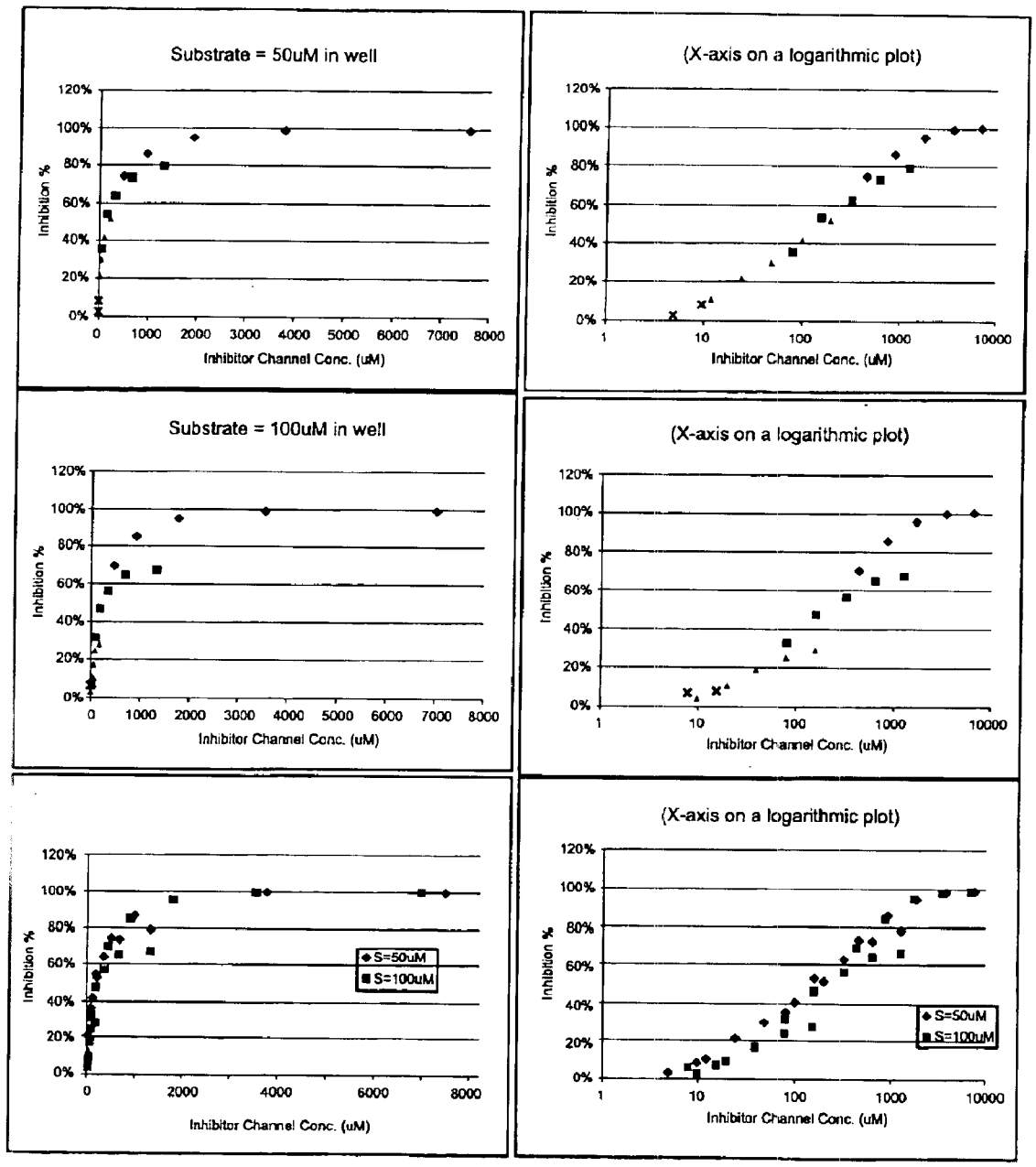
FIG. 17: Enzyme inhibition assay data showing inhibitor channel concentration vs. percent inhibition.

Inhibitor titration measured in 4 different assay channels using 2 different substrate concentrations is shown in FIG. 15. The Dixon plot used to determine $K_i$ is shown in FIG. 16 and FIG. 17, which provide inhibitor channel concentration data plotted against percent inhibition.

Example 2

Suppression of Pressure Perturbations

Figure 10:
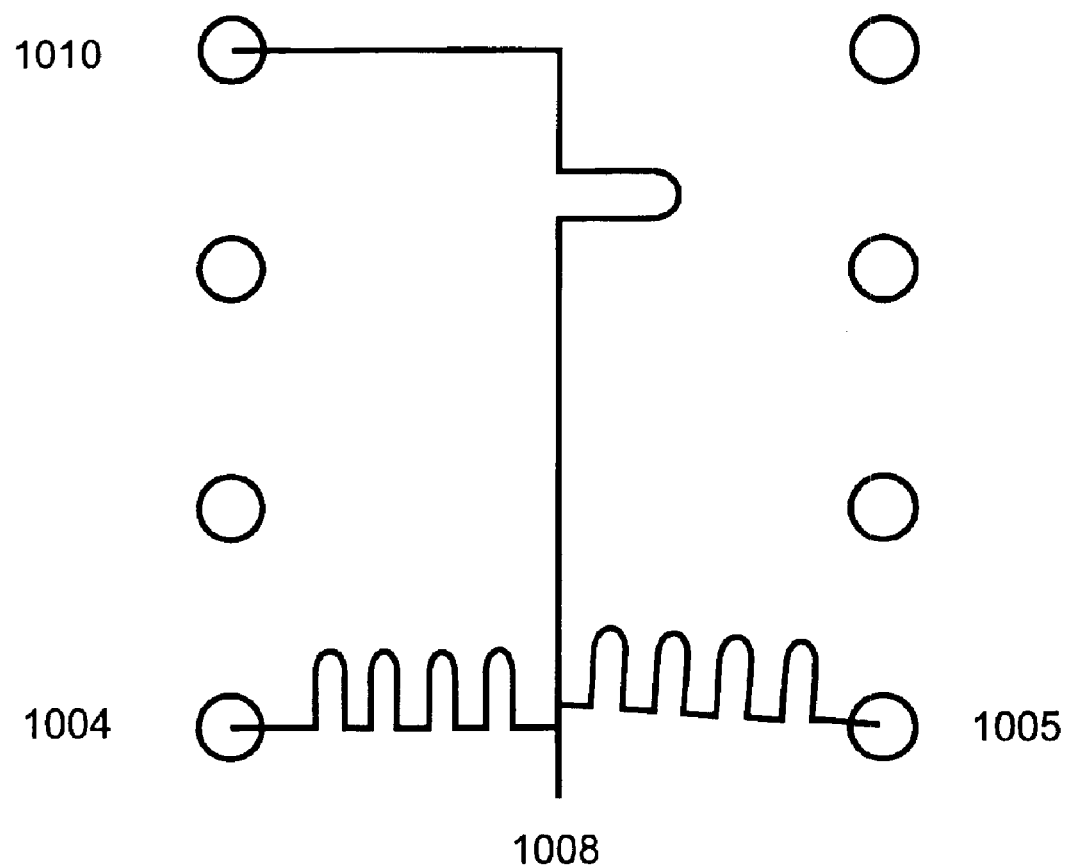
FIG. 10: A channel configuration for a microfluidic sipper device without a shunt channel.

A microfluidic device comprising the channel layout shown in FIG. 10, is typically used for high throughput screening assays, e.g., fluorogenic assays. In a typical experiment, an enzyme is placed in well 1004 and a fluorogenic substrate is placed in well 1005. Potential inhibitors are placed in a microwell plate and brought onto the device through a capillary attached to the device at capillary connection point 1008. As described above, spontaneous injection occurs as the capillary is lifted from one well in the microwell plate and moved to another well. The effect of spontaneous injection on the dilution factor for the reagents added from internal wells, e.g., wells 1004 and 1005, is characterized by placing a dye, e.g., a fluorescent dye, in a buffer solution in wells 1004 and 1005 on the device and moving the capillary back and forth between 2 microplate wells containing the same buffer solution.

Figure 11:
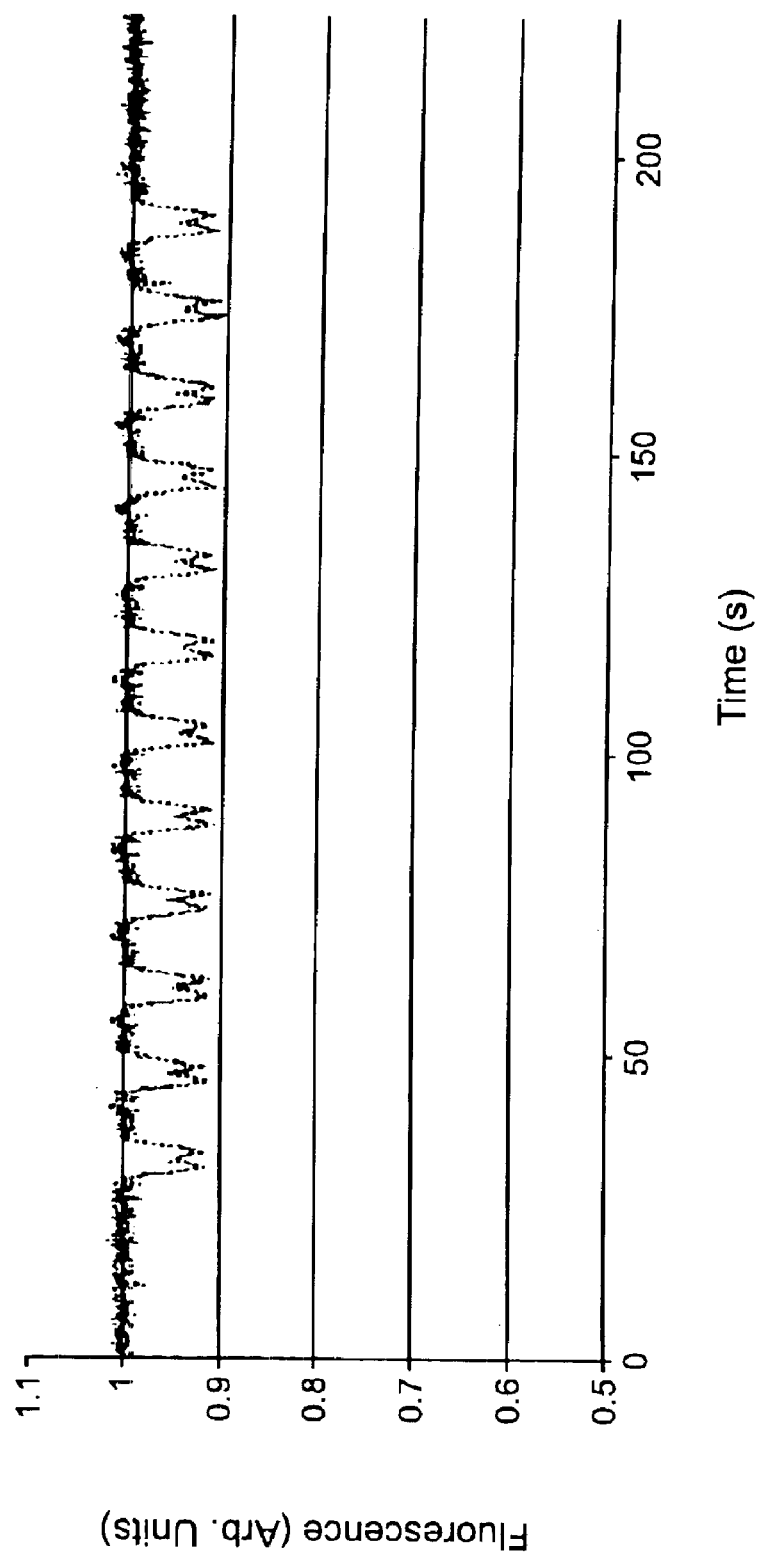
FIG. 11: Data showing the spontaneous injection perturbations observed using the microfluidic device of FIG. 10.

FIG. 11 provides the corresponding fluorescent signal measured when a vacuum positioned at waste well 1010 is set at −1 psi. The double dip feature in the data results from the perturbation to the steady state value due to spontaneous injection of buffer from the capillary into the microfluidic device. The magnitude of the dips is about 9% of the steady state value.

Figure 12:
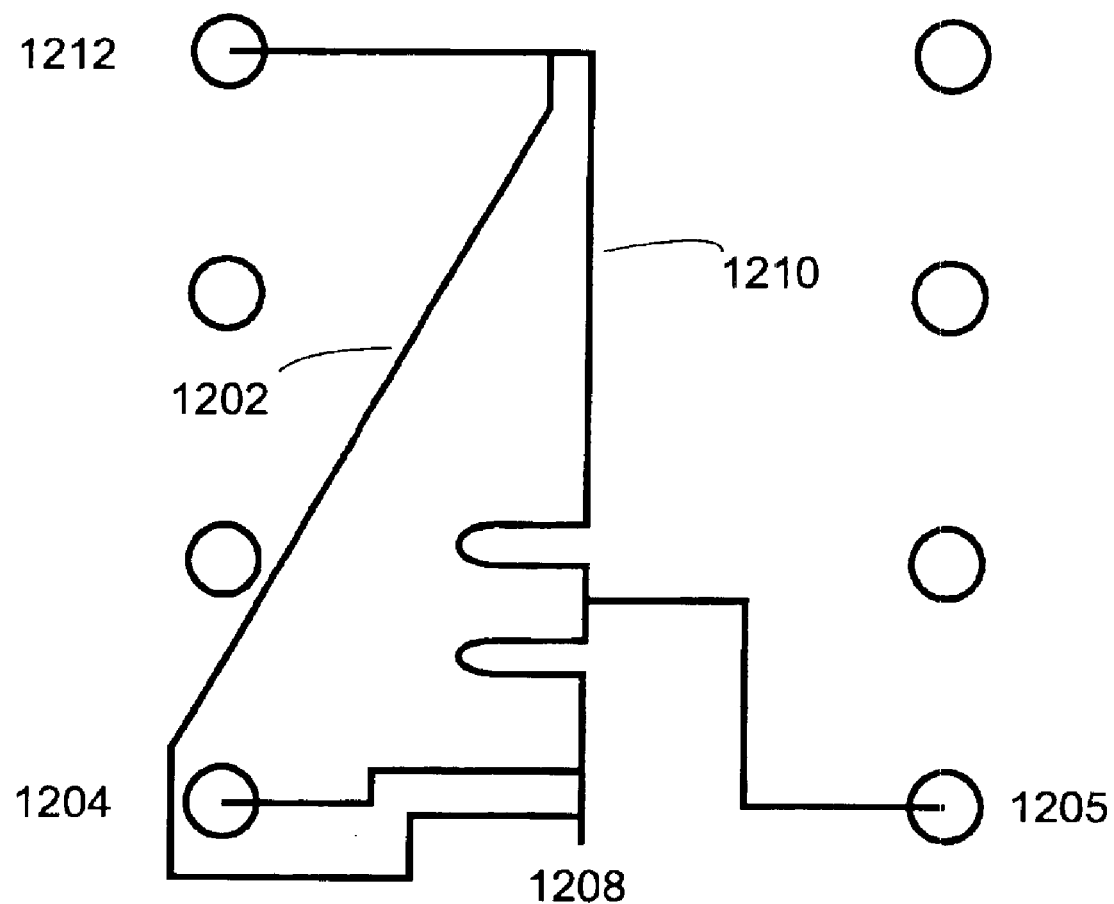
FIG. 12: A channel configuration for a microfluidic sipper device comprising a shunt channel.

The microfluidic device channel layout shown in FIG. 12 contains a modification that is optionally used to suppress the pressure perturbations described above and illustrated by the data in FIG. 11. The channel configuration contains a by-pass or shunt channel 1202 used to draw fluid from main channel 1210. A fluorogenic assay is optionally performed in the device of FIG. 12 in the same manner as that described above for the device in FIG. 10. Enzyme and substrate are introduced into main channel 1210 from wells 1204 and 1205. In main channel 1210, the enzyme and substrate contact a sample brought in from an external capillary via capillary connection point 1208. Pressure at capillary connection point 1208 is controlled by the shunting of fluid from main channel 1210 to shunt channel 1202.

Flowing fluid through shunt channel 1204 alters the pressure at the intersection point to reduce the effect of spontaneous injection. For example, when characterized using the dyes and buffers as described above for the device of FIG. 10, the signal produced using the device of FIG. 12 results in dips having a magnitude that is only 3% of the steady state value.

Figure 13:
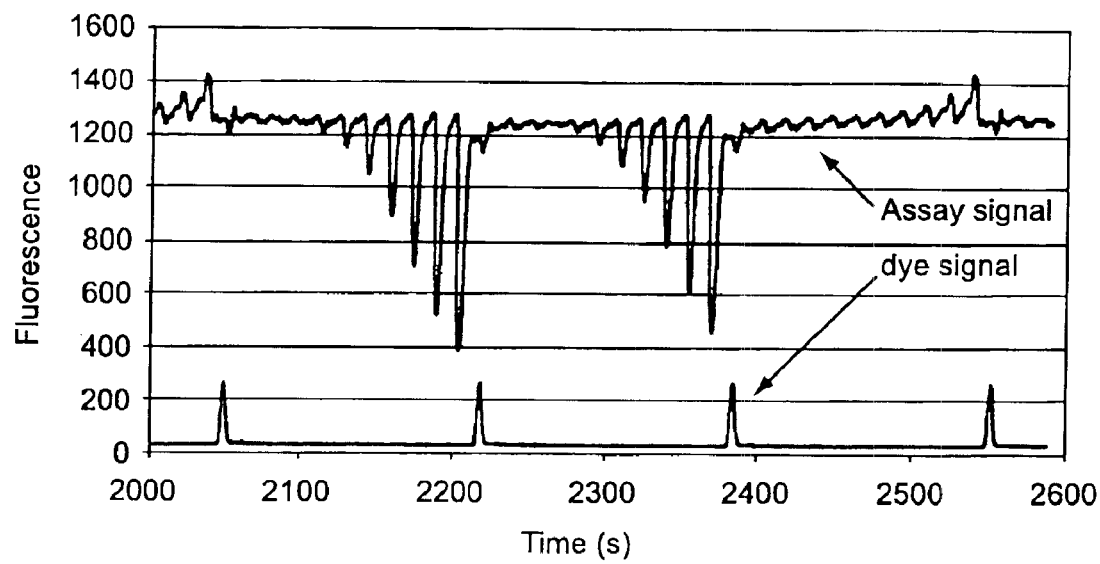
FIG. 13: Enzyme inhibition data obtained using the device of FIG. 10, the device without a shunt channel.
Figure 14:
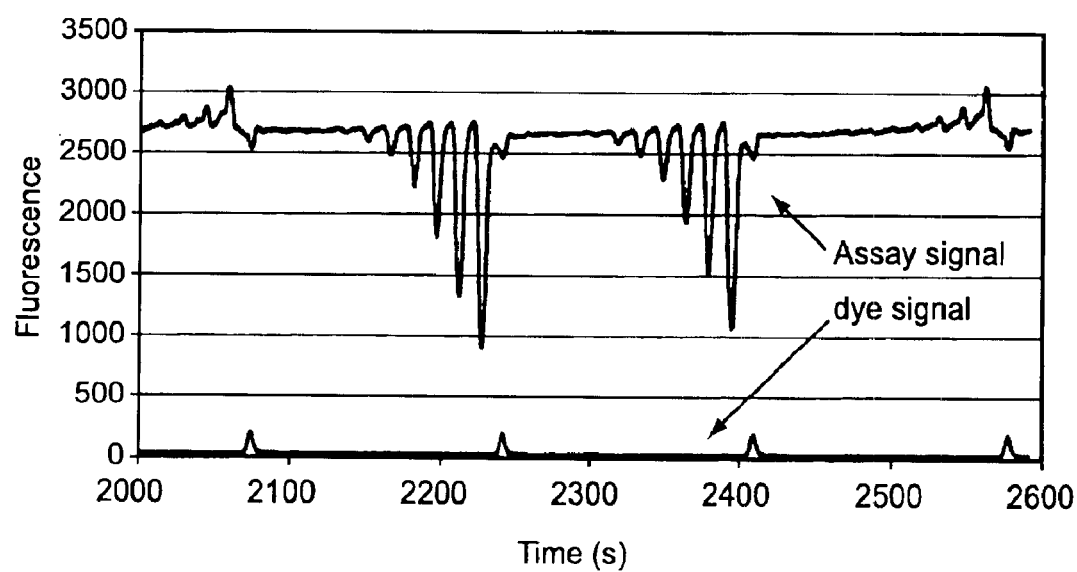
FIG. 14: Enzyme inhibition data obtained using the device of FIG. 12, the device comprising a shunt channel.

FIGS. 13 and 14 provide data for a fluorogenic enzyme assay performed using a device without a shunt channel (FIG. 10) and a device with a shunt channel (FIG. 12), respectively. An approximately 10 nM solution of a phosphatase enzyme was placed in well 1204 and 100 μM phosphatase substrate was placed in well 1205. The buffer used was 50 MM Bis-Tris at pH 6.3, 50 mM NaCl, 0.075% BSA, 0.1% Brij-35, and 2% DMSO. Inhibitors of phosphatases were provided at 10 different concentrations: 0.156, 0.313, 0.625, 1.25, 5, 10, 20, 40, and 80 μM. The inhibitor samples were placed in a microwell plate and flowed into the device from the microwell plate via a sipper capillary attached at capillary connection point 1208. Applied pressure was set at −1.5 psi at waste reservoir 1212. The periodic wiggles or dips in the steady state signal due to spontaneous injection were much reduced in amplitude in the device comprising a shunt channel.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patent applications, patents, and other documents cited in this application are incorporated by reference in their entirety for all purposes to the same extent as if each individual publication or patent document were individually so denoted.

What is claimed is:

1. A method of diluting a first fluid in a microfluidic device, comprising:
   (i) providing a microfluidic device including a body structure comprising a plurality of microscale channels disposed therein, the plurality of microscale channels comprising:

(a) at least a first main channel; and, (b) a plurality of flow reduction channels each having a first and second end, wherein the first end of each of the plurality of flow reduction channels intersects the first main channel, and wherein the second ends of all of the plurality of flow reduction channels are fluidly coupled to a single, common fluid reservoir;

(ii) introducing a first fluid into the first main channel;

(iii) introducing a second fluid into the first main channel, the first and second fluids mixing in the first main channel;

(iv) removing a portion of the first and second fluids mixed in the first main channel through a first one of the plurality of flow reduction channels;

(v) introducing at least a third fluid into the first main channel to mix with the first and second fluids mixed in the first channel; and (vi) removing a portion of the first, second and third fluids mixed in the first channel through a second one of the plurality of flow reduction channels, thereby diluting the first fluid with the second and third fluids in the first main channel;

wherein at least steps (iv) and (vi) are performed by applying a pressure or vacuum to the common fluid reservoir.

2. The method of claim 1, wherein the first main channel has a first cross-sectional dimension and the plurality of flow reduction channels each have a second cross-sectional dimension, wherein the first cross-sectional dimension and the second cross-sectional dimension are different.

3. The method of claim 2, wherein the second cross-sectional dimension is smaller than the first cross-sectional dimension.

4. The method of claim 1, further comprising providing a pressure source operably coupled to the common fluid reservoir.

5. The method of claim 4, wherein the pressure source comprises a vacuum source.

6. The method of claim 5, wherein the pressure source comprises a single vacuum source.

7. The method of claim 5, wherein steps (ii), (iii), (iv), (v) and (vi) are performed by applying a pressure or vacuum to the common fluid reservoir.

8. The method of claim 1, wherein the second ends of all of the plurality of flow reduction channels intersect the first main channel.

9. The method of claim 1, wherein the second ends of all of the plurality of flow reduction channels intersect the first main channel at a location which is downstream from a detection region located along a length of the first main channel.

10. The method of claim 1, wherein the plurality of flow reduction channels are each proximal to a respective detection region.

11. The method of claim 1, further comprising providing in the body structure secondary flow reduction channel fluidly coupled to one of the plurality of flow reduction channels, the secondary flow reduction channel having a first end which intersects the one of the plurality of flow reduction channels, and a second end which is fluidly coupled to the common fluid reservoir.

12. The method of claim 11, further comprising:

(vii) introducing a fourth fluid into the main channel, the first, second, third, and fourth fluids mixing in the main channel; and (viii) removing a portion of the first, second, third, and fourth fluids mixed in the main channel through the first end of a third one of the plurality of flow reduction channels.

13. The method of claim 12, wherein at least step (viii) is performed by applying a vacuum to the common fluid reservoir.

* * * * *